United States Patent
Dakin et al.

(10) Patent No.: US 8,690,816 B2
(45) Date of Patent: *Apr. 8, 2014

(54) IMPLANTABLE FLOW CONNECTOR

(75) Inventors: Adam Dakin, Blue Bell, PA (US);
Michael Dugery, Doylestown, PA (US);
Todd Polk, Doylestown, PA (US);
Richard Briganti, Philadelphia, PA (US); Michael Paris, Landsdale, PA (US); Nicholas Gately, Lambertville, NJ (US); Zaw N. Win, Philadelphia, PA (US)

(73) Assignee: Bioconnect Systems, Inc., Ambler, PA (US)

( * ) Notice: Subject to any disclaimer, the term of this patent is extended or adjusted under 35 U.S.C. 154(b) by 614 days.

This patent is subject to a terminal disclaimer.

(21) Appl. No.: 12/185,810

(22) Filed: Aug. 4, 2008

(65) Prior Publication Data

US 2009/0036820 A1    Feb. 5, 2009

Related U.S. Application Data

(60) Provisional application No. 60/953,570, filed on Aug. 2, 2007.

(51) Int. Cl.
*A61B 19/00*    (2006.01)

(52) U.S. Cl.
USPC ............................................ 604/8; 604/264

(58) Field of Classification Search
USPC ................. 604/8, 9, 264; 623/1.3, 1.31, 1.36, 623/23.64; 606/153
See application file for complete search history.

(56) References Cited

U.S. PATENT DOCUMENTS

| | | | |
|---|---|---|---|
| 2,127,903 A | | 8/1938 | Bowen |
| 3,818,511 A | * | 6/1974 | Goldberg et al. ............ 623/1.31 |
| 3,974,835 A | | 8/1976 | Hardy, Jr. |
| 4,352,358 A | | 10/1982 | Angelchik |
| 4,366,819 A | | 1/1983 | Kaster |
| 4,368,736 A | | 1/1983 | Kaster |
| 4,667,673 A | | 5/1987 | Li |
| 4,705,040 A | | 11/1987 | Mueller et al. |
| 4,744,364 A | | 5/1988 | Kensey |
| 4,787,386 A | | 11/1988 | Walsh et al. |
| 4,852,568 A | | 8/1989 | Kensey |
| 4,890,612 A | | 1/1990 | Kensey |

(Continued)

FOREIGN PATENT DOCUMENTS

| | | |
|---|---|---|
| EP | 0894975 | 2/1999 |
| JP | 03-018355 | 1/1991 |

(Continued)

*Primary Examiner* — Leslie Deak

(57) ABSTRACT

An implantable flow connector for fluidically coupling a source tissue-enclosed body space with a destination element, comprising: a conduit having a lumen terminating at an orifice at a first end of the conduit implantable in the source body space through an opening formed in a tissue wall of the source body space, and a second end of the conduit implantable in the destination element through an opening in a surface of the destination element; and a circumferential flange, radially extending from the conduit proximate the conduit first end, configured to be implanted in the source body space adjacent an opening in the tissue wall of the source body space such that the conduit extends through the opening, the flange comprising one or more circumferentially adjacent sections at least one of which has a rigidity that decreases in a radially-increasing direction.

69 Claims, 32 Drawing Sheets

(56) References Cited

U.S. PATENT DOCUMENTS

| | | | |
|---|---|---|---|
| 5,061,274 A | 10/1991 | Kensey | |
| 5,108,421 A | 4/1992 | Fowler | |
| 5,141,516 A | 8/1992 | Detweiler | |
| 5,156,619 A * | 10/1992 | Ehrenfeld | 623/1.31 |
| 5,192,302 A | 3/1993 | Kensey et al. | |
| 5,197,976 A | 3/1993 | Herweck et al. | |
| 5,222,974 A | 6/1993 | Kensey et al. | |
| 5,282,827 A | 2/1994 | Kensey et al. | |
| 5,330,445 A | 7/1994 | Haaga | |
| 5,453,090 A | 9/1995 | Martinez et al. | |
| 5,456,714 A * | 10/1995 | Owen | 623/1.31 |
| 5,503,635 A | 4/1996 | Sauer et al. | |
| 5,549,633 A | 8/1996 | Evans et al. | |
| 5,586,987 A | 12/1996 | Fahy | |
| 5,620,461 A | 4/1997 | VanDe Moer et al. | |
| 5,634,936 A | 6/1997 | Linden et al. | |
| 5,643,340 A | 7/1997 | Nunokawa | |
| 5,649,959 A | 7/1997 | Hannam et al. | |
| 5,669,924 A | 9/1997 | Shaknovich | |
| 5,676,670 A | 10/1997 | Kim | |
| 5,683,451 A | 11/1997 | Lenker et al. | |
| 5,702,414 A | 12/1997 | Richter et al. | |
| 5,716,325 A | 2/1998 | Bonutti | |
| 5,728,134 A | 3/1998 | Barak | |
| 5,755,778 A | 5/1998 | Kleshinski | |
| 5,796,178 A | 8/1998 | Onuma | |
| 5,797,934 A | 8/1998 | Rygaard | |
| 5,817,113 A | 10/1998 | Gifford, III et al. | |
| 5,830,222 A | 11/1998 | Makower | |
| 5,853,422 A | 12/1998 | Huebsch et al. | |
| 5,868,697 A | 2/1999 | Richter et al. | |
| 5,868,761 A | 2/1999 | Nicholas et al. | |
| 5,868,763 A | 2/1999 | Spence et al. | |
| 5,868,777 A | 2/1999 | Lam | |
| 5,893,886 A * | 4/1999 | Zegdi et al. | 623/1.1 |
| 5,921,995 A | 7/1999 | Kleshinski | |
| 5,922,022 A | 7/1999 | Nash et al. | |
| 6,007,544 A | 12/1999 | Kim | |
| 6,007,576 A * | 12/1999 | McClellan | 623/23.64 |
| 6,017,352 A | 1/2000 | Nash et al. | |
| 6,019,788 A | 2/2000 | Butters et al. | |
| 6,030,395 A | 2/2000 | Nash et al. | |
| 6,036,702 A | 3/2000 | Bachinski et al. | |
| 6,036,705 A | 3/2000 | Nash et al. | |
| 6,056,762 A | 5/2000 | Nash et al. | |
| 6,063,114 A | 5/2000 | Nash et al. | |
| 6,068,638 A | 5/2000 | Makower | |
| 6,068,654 A | 5/2000 | Berg et al. | |
| 6,071,297 A | 6/2000 | Salahieh et al. | |
| 6,077,291 A | 6/2000 | Das | |
| 6,113,612 A | 9/2000 | Swanson et al. | |
| 6,117,145 A | 9/2000 | Wood et al. | |
| 6,149,681 A | 11/2000 | Houser et al. | |
| 6,152,937 A | 11/2000 | Peterson et al. | |
| 6,152,945 A | 11/2000 | Bachinski et al. | |
| 6,165,185 A | 12/2000 | Shennib et al. | |
| 6,171,329 B1 | 1/2001 | Shaw et al. | |
| 6,176,864 B1 | 1/2001 | Chapman | |
| 6,190,353 B1 | 2/2001 | Makower et al. | |
| 6,190,397 B1 | 2/2001 | Spence et al. | |
| 6,193,734 B1 | 2/2001 | Bolduc et al. | |
| 6,203,513 B1 | 3/2001 | Yaron et al. | |
| 6,206,893 B1 | 3/2001 | Klein et al. | |
| 6,206,913 B1 | 3/2001 | Yencho et al. | |
| 6,214,022 B1 | 4/2001 | Taylor et al. | |
| 6,214,029 B1 | 4/2001 | Thill et al. | |
| 6,217,585 B1 | 4/2001 | Houser et al. | |
| 6,231,587 B1 | 5/2001 | Makower | |
| 6,241,741 B1 | 6/2001 | Duhaylongsod et al. | |
| 6,241,768 B1 | 6/2001 | Agarwal et al. | |
| 6,251,116 B1 | 6/2001 | Shennib et al. | |
| 6,254,630 B1 | 7/2001 | Inoue | |
| 6,270,515 B1 | 8/2001 | Linden et al. | |
| 6,283,983 B1 | 9/2001 | Makower et al. | |
| 6,293,955 B1 | 9/2001 | Houser et al. | |
| 6,302,905 B1 | 10/2001 | Goldsteen et al. | |
| 6,350,280 B1 | 2/2002 | Nash et al. | |
| 6,371,965 B2 | 4/2002 | Gifford, III et al. | |
| 6,391,038 B2 | 5/2002 | Vargas et al. | |
| 6,395,015 B1 * | 5/2002 | Borst et al. | 606/213 |
| 6,395,019 B2 | 5/2002 | Chobotov | |
| 6,398,797 B2 | 6/2002 | Bombard et al. | |
| 6,402,764 B1 | 6/2002 | Hendricksen et al. | |
| 6,402,767 B1 | 6/2002 | Nash et al. | |
| 6,409,739 B1 | 6/2002 | Nobles et al. | |
| 6,419,681 B1 | 7/2002 | Vargas et al. | |
| 6,428,550 B1 | 8/2002 | Vargas et al. | |
| 6,440,163 B1 | 8/2002 | Swanson et al. | |
| 6,443,965 B1 | 9/2002 | Gifford, III et al. | |
| 6,451,048 B1 | 9/2002 | Berg et al. | |
| 6,458,140 B2 | 10/2002 | Akin et al. | |
| 6,461,320 B1 | 10/2002 | Yencho et al. | |
| 6,464,709 B1 | 10/2002 | Shennib et al. | |
| 6,471,713 B1 | 10/2002 | Vargas et al. | |
| 6,478,817 B2 | 11/2002 | Schmitt et al. | |
| 6,485,496 B1 | 11/2002 | Suyker et al. | |
| 6,485,513 B1 | 11/2002 | Fan | |
| 6,494,889 B1 | 12/2002 | Fleischman et al. | |
| 6,497,710 B2 | 12/2002 | Yencho et al. | |
| 6,508,824 B1 | 1/2003 | Flaherty et al. | |
| 6,517,558 B2 | 2/2003 | Gittings et al. | |
| 6,537,287 B1 | 3/2003 | Yencho et al. | |
| 6,537,288 B2 | 3/2003 | Vargas et al. | |
| 6,554,764 B1 | 4/2003 | Vargas et al. | |
| 6,565,581 B1 | 5/2003 | Spence et al. | |
| 6,582,463 B1 * | 6/2003 | Mowry et al. | 623/1.35 |
| 6,585,762 B1 | 7/2003 | Stanish | |
| 6,589,277 B1 * | 7/2003 | Fabiani et al. | 623/1.31 |
| 6,589,278 B1 | 7/2003 | Harris et al. | |
| 6,599,302 B2 | 7/2003 | Houser et al. | |
| 6,602,263 B1 | 8/2003 | Swanson et al. | |
| 6,616,675 B1 | 9/2003 | Evard et al. | |
| 6,620,129 B2 | 9/2003 | Stecker et al. | |
| 6,626,920 B2 | 9/2003 | Whayne | |
| 6,626,939 B1 | 9/2003 | Burnside et al. | |
| 6,648,900 B2 | 11/2003 | Fleischman et al. | |
| 6,648,901 B2 * | 11/2003 | Fleischman et al. | 606/155 |
| 6,652,543 B2 | 11/2003 | Spence et al. | |
| 6,655,386 B2 | 12/2003 | Makower et al. | |
| 6,673,085 B1 | 1/2004 | Berg | |
| 6,695,875 B2 | 2/2004 | Stelter et al. | |
| 6,699,257 B2 | 3/2004 | Gifford, III et al. | |
| 6,702,828 B2 | 3/2004 | Whayne | |
| 6,709,441 B2 | 3/2004 | Bolduc et al. | |
| 6,712,831 B1 | 3/2004 | Kaplan et al. | |
| 6,719,769 B2 | 4/2004 | Donohoe et al. | |
| 6,719,781 B1 | 4/2004 | Kim | |
| 6,726,697 B2 | 4/2004 | Nicholas et al. | |
| 6,736,825 B2 | 5/2004 | Blatter et al. | |
| 6,740,101 B2 | 5/2004 | Houser et al. | |
| 6,743,243 B1 | 6/2004 | Roy et al. | |
| 6,776,785 B1 | 8/2004 | Yencho et al. | |
| 6,786,914 B1 | 9/2004 | Vargas et al. | |
| 6,790,229 B1 | 9/2004 | Berreklouw | |
| 6,821,286 B1 | 11/2004 | Carranza et al. | |
| 6,858,035 B2 | 2/2005 | Whayne | |
| 6,866,674 B2 | 3/2005 | Galdonik et al. | |
| 6,869,437 B1 | 3/2005 | Hausen et al. | |
| 6,893,449 B2 | 5/2005 | Vargas et al. | |
| 6,905,504 B1 | 6/2005 | Vargas | |
| 6,911,042 B2 | 6/2005 | Weadock | |
| 6,913,607 B2 | 7/2005 | Ainsworth et al. | |
| 6,913,609 B2 | 7/2005 | Yencho et al. | |
| 6,916,327 B2 | 7/2005 | Northrup, III et al. | |
| 6,926,690 B2 | 8/2005 | Renati | |
| 6,926,724 B1 | 8/2005 | Chu | |
| 6,942,675 B1 | 9/2005 | Vargas | |
| 6,962,596 B2 | 11/2005 | Bolduc et al. | |
| 6,972,023 B2 | 12/2005 | Whayne et al. | |
| 7,008,436 B2 | 3/2006 | Barath | |
| 7,018,388 B2 | 3/2006 | Yencho et al. | |
| 7,025,773 B2 | 4/2006 | Gittings et al. | |
| 7,029,482 B1 | 4/2006 | Vargas et al. | |
| 7,041,110 B2 | 5/2006 | Yencho et al. | |

(56) References Cited

U.S. PATENT DOCUMENTS

| | | |
|---|---|---|
| 7,041,112 B2 | 5/2006 | Vargas et al. |
| 7,063,712 B2 | 6/2006 | Vargas et al. |
| 7,128,749 B1 | 10/2006 | Vargas et al. |
| 7,160,311 B2 | 1/2007 | Blatter et al. |
| 7,172,608 B2 | 2/2007 | Vargas et al. |
| 7,175,637 B2 | 2/2007 | Vargas et al. |
| 7,270,670 B1 | 9/2007 | Yencho |
| 7,285,131 B1 | 10/2007 | Bombard et al. |
| 7,291,157 B1 | 11/2007 | Hausen et al. |
| 7,300,444 B1 | 11/2007 | Nielsen et al. |
| 7,303,569 B2 | 12/2007 | Yencho et al. |
| 7,303,570 B2 | 12/2007 | Bombard et al. |
| 7,309,343 B2 | 12/2007 | Vargas et al. |
| 7,351,247 B2 | 4/2008 | Kupiecki |
| 7,371,243 B1 | 5/2008 | Nielsen et al. |
| 7,427,261 B1 | 9/2008 | Carranza et al. |
| 7,666,197 B2 | 2/2010 | Orban, III |
| 7,766,924 B1 | 8/2010 | Bombard et al. |
| 7,794,471 B1 | 9/2010 | Bender et al. |
| 7,892,246 B2 | 2/2011 | Akin |
| 7,892,247 B2 | 2/2011 | Conston |
| 7,922,733 B2 | 4/2011 | Borghi |
| 8,052,741 B2 | 11/2011 | Bruszewski et al. |
| 8,105,345 B2 | 1/2012 | Golden et al. |
| 8,142,387 B2 | 3/2012 | Heise et al. |
| 8,182,494 B1 | 5/2012 | Yencho et al. |
| 8,353,920 B2 | 1/2013 | Mikkaichi |
| 8,353,921 B2 | 1/2013 | Schaller et al. |
| 8,361,092 B1 | 1/2013 | Asfora |
| 8,366,651 B2 | 2/2013 | Dakin et al. |
| 2001/0004699 A1 | 6/2001 | Gittings et al. |
| 2001/0047165 A1 | 11/2001 | Makower et al. |
| 2001/0049539 A1 | 12/2001 | Rehil |
| 2002/0022853 A1 | 2/2002 | Swanson et al. |
| 2002/0029079 A1 | 3/2002 | Kim et al. |
| 2002/0091398 A1 | 7/2002 | Galdonik et al. |
| 2003/0028205 A1 | 2/2003 | Vargas et al. |
| 2003/0065344 A1 | 4/2003 | Kirsch et al. |
| 2003/0212418 A1 | 11/2003 | Yencho et al. |
| 2003/0225425 A1 | 12/2003 | Kupiecki et al. |
| 2003/0229365 A1 | 12/2003 | Whayne et al. |
| 2003/0236542 A1 | 12/2003 | Makower |
| 2004/0024345 A1 | 2/2004 | Gharib et al. |
| 2004/0044349 A1 | 3/2004 | Barry et al. |
| 2004/0049212 A1 | 3/2004 | Whayne |
| 2004/0073282 A1 | 4/2004 | Stanish |
| 2004/0087985 A1 | 5/2004 | Loshakove et al. |
| 2004/0088042 A1 | 5/2004 | Kim et al. |
| 2004/0092975 A1 | 5/2004 | Loshakove et al. |
| 2004/0097991 A1 | 5/2004 | Vargas et al. |
| 2004/0102796 A1 | 5/2004 | Hill et al. |
| 2004/0122318 A1 | 6/2004 | Flaherty et al. |
| 2004/0133225 A1 | 7/2004 | Makower |
| 2004/0158143 A1 | 8/2004 | Flaherty et al. |
| 2004/0158267 A1 | 8/2004 | Sancoff et al. |
| 2004/0249400 A1 | 12/2004 | Vargas et al. |
| 2004/0249415 A1 | 12/2004 | Vargas et al. |
| 2004/0260318 A1 | 12/2004 | Hunter et al. |
| 2005/0033329 A1 | 2/2005 | Bombard et al. |
| 2005/0043751 A1 | 2/2005 | Phan et al. |
| 2005/0043752 A1 | 2/2005 | Phan et al. |
| 2005/0137614 A1 | 6/2005 | Porter et al. |
| 2005/0149073 A1 | 7/2005 | Arani et al. |
| 2005/0165426 A1 | 7/2005 | Manzo |
| 2005/0192604 A1 | 9/2005 | Carson et al. |
| 2005/0251163 A1 | 11/2005 | Tilson |
| 2005/0251180 A1 | 11/2005 | Burton et al. |
| 2005/0251187 A1 | 11/2005 | Beane et al. |
| 2006/0025788 A1 | 2/2006 | Loshakove et al. |
| 2006/0064119 A9 | 3/2006 | Tilson et al. |
| 2006/0241342 A1 | 10/2006 | Macaulay et al. |
| 2007/0005128 A1* | 1/2007 | Scholz et al. ............... 623/1.31 |
| 2007/0027526 A1 | 2/2007 | Demetriades et al. |
| 2007/0156079 A1 | 7/2007 | Brown |
| 2007/0282245 A1 | 12/2007 | Tu et al. |
| 2008/0009889 A1 | 1/2008 | Pokorney et al. |
| 2008/0009936 A1 | 1/2008 | Kim et al. |
| 2008/0262604 A1 | 10/2008 | Stengel |
| 2009/0036817 A1* | 2/2009 | Dakin et al. ..................... 604/8 |
| 2009/0036820 A1 | 2/2009 | Dakin et al. |
| 2009/0076531 A1 | 3/2009 | Richardson |
| 2009/0143793 A1 | 6/2009 | Chua et al. |
| 2010/0130995 A1 | 5/2010 | Yevzlin et al. |
| 2011/0118764 A1 | 5/2011 | Beane et al. |
| 2011/0184329 A1 | 7/2011 | Kramer et al. |
| 2012/0065652 A1 | 3/2012 | Cully et al. |
| 2012/0123451 A1 | 5/2012 | Asfora et al. |

FOREIGN PATENT DOCUMENTS

| | | |
|---|---|---|
| JP | 09-511409 | 11/1997 |
| JP | 02003220065 | 8/2003 |
| WO | WO-90/14796 | 12/1990 |
| WO | 9514442 | 6/1995 |
| WO | 9727898 | 8/1997 |
| WO | WO97/31590 | 9/1997 |
| WO | 9802099 | 1/1998 |
| WO | 9807970 | 2/1998 |
| WO | 9816174 | 4/1998 |
| WO | 9819629 | 5/1998 |
| WO | 9819636 | 5/1998 |
| WO | 9840036 | 9/1998 |
| WO | 9852471 | 11/1998 |
| WO | 9852474 | 11/1998 |
| WO | WO98/52495 | 11/1998 |
| WO | WO-99/08603 | 2/1999 |
| WO | 9911180 | 3/1999 |
| WO | 9948427 | 9/1999 |
| WO | 0027310 | 5/2000 |
| WO | 0027313 | 5/2000 |
| WO | 0041633 | 7/2000 |
| WO | WO-00/49951 | 8/2000 |
| WO | 0053104 | 9/2000 |
| WO | WO-00/69365 | 11/2000 |
| WO | WO01/17440 | 3/2001 |
| WO | 0139672 | 6/2001 |
| WO | 0141653 | 6/2001 |
| WO | 02058591 | 8/2002 |

* cited by examiner

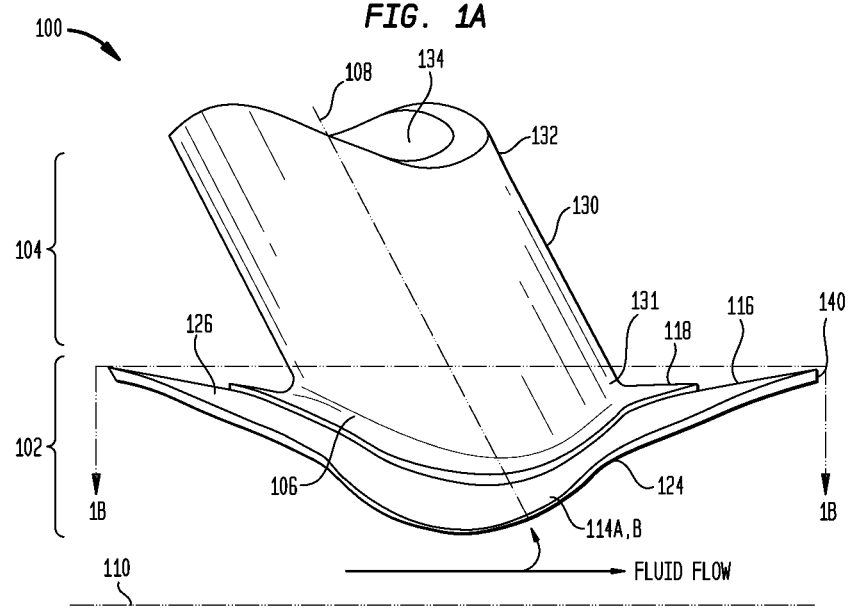
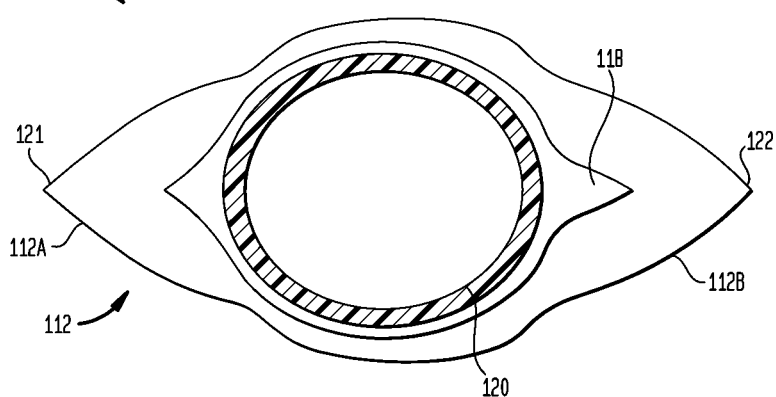

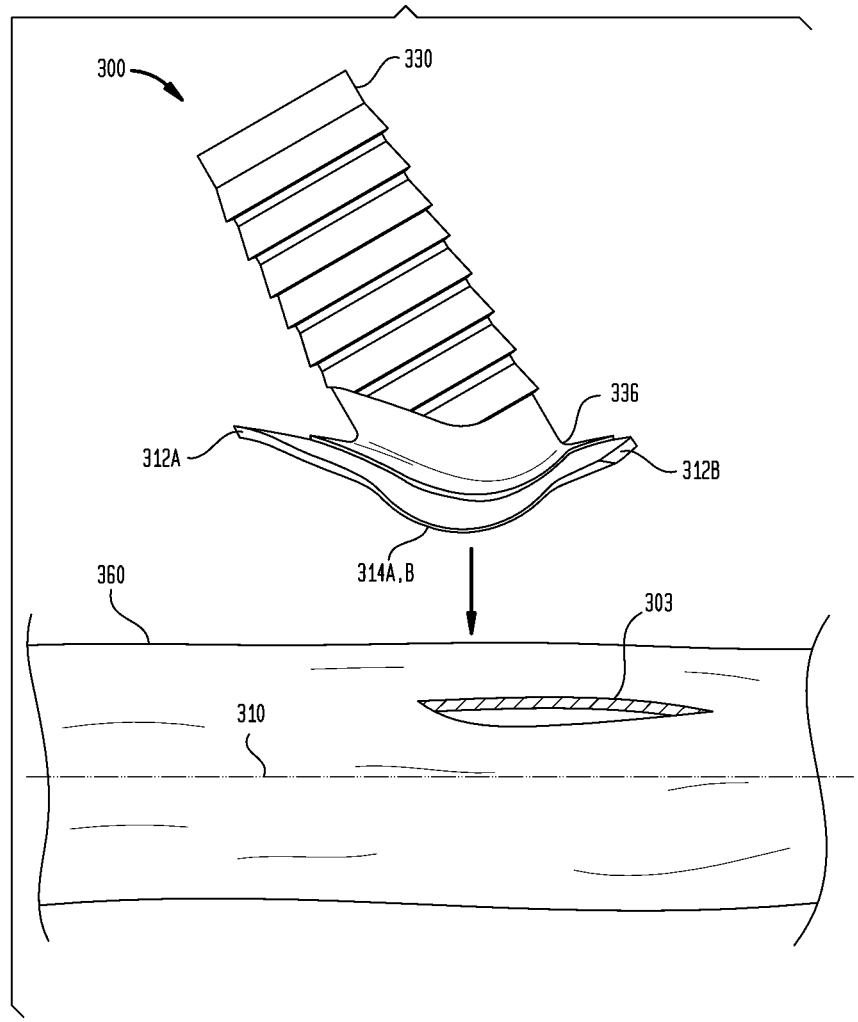

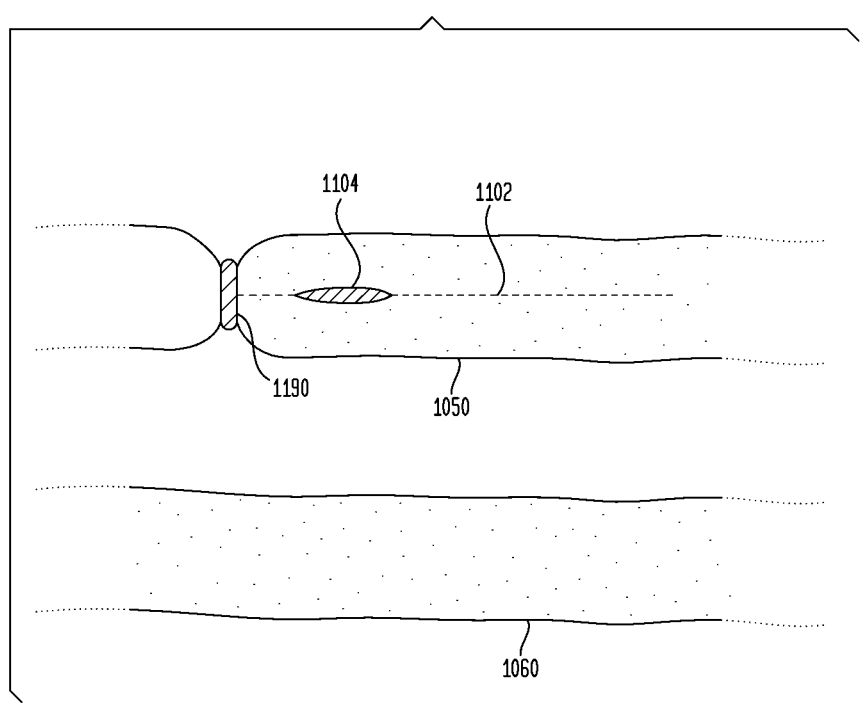

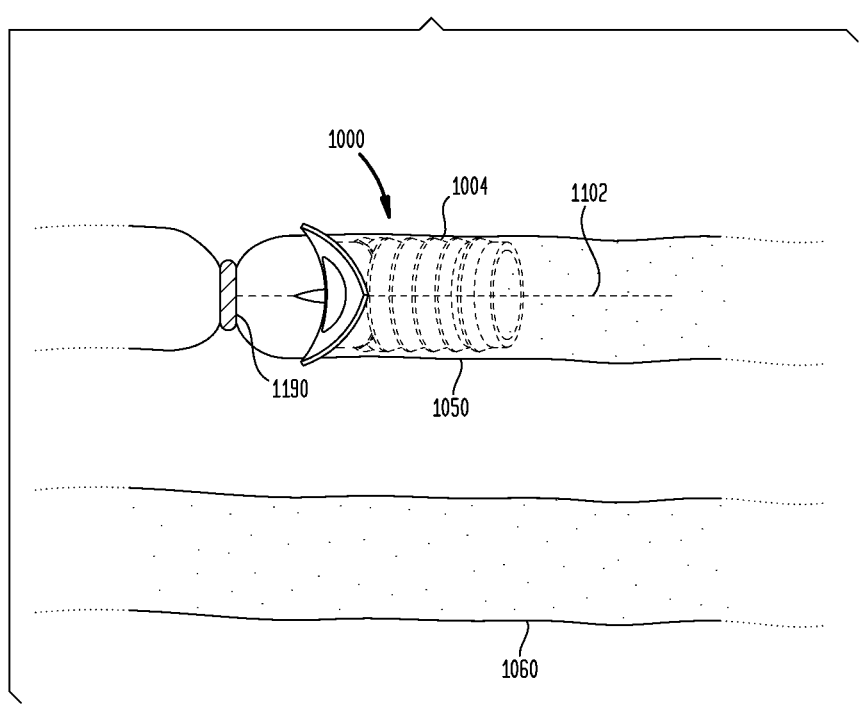

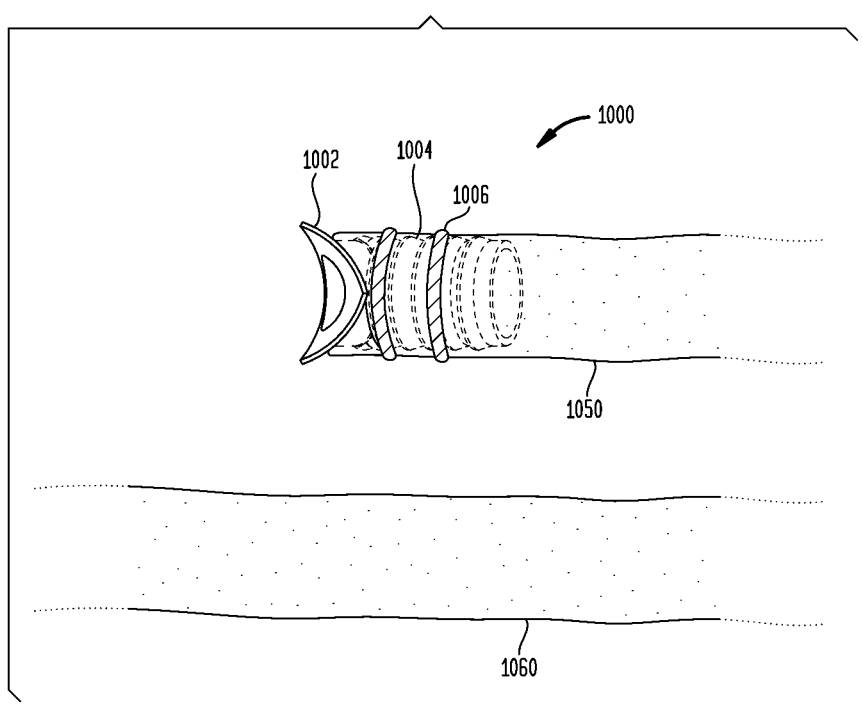

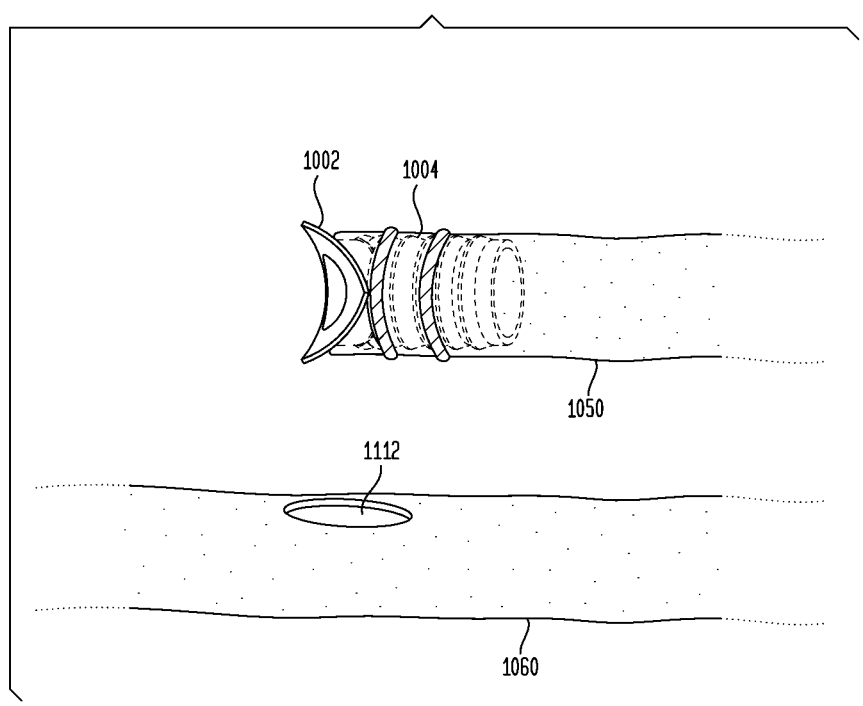

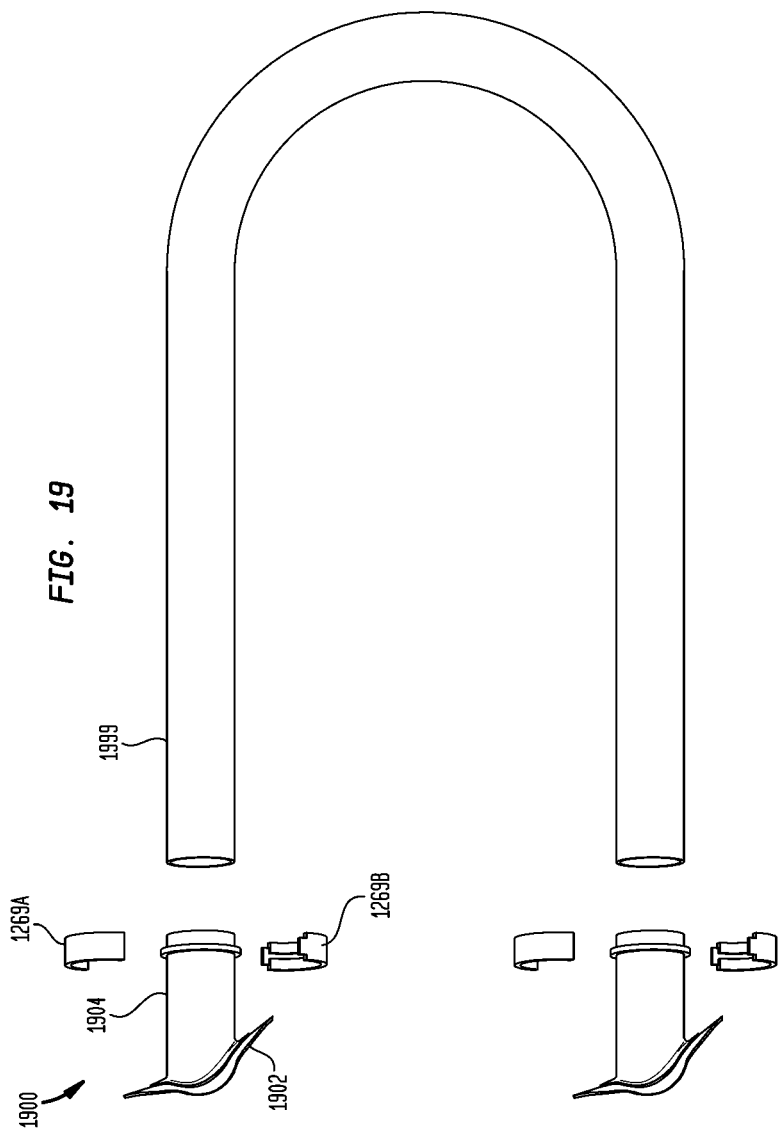

IMPLANTABLE FLOW CONNECTOR

CROSS-REFERENCE TO RELATED APPLICATIONS

This application claims the benefit of U.S. Provisional Application No. 60/953,570, entitled "Device for Interconnecting Internal Passageways in a Patient," filed Aug. 2, 2007. This application is hereby incorporated by reference herein.

BACKGROUND

1. Field of the Invention

The present invention relates generally to implantable medical devices and, more particularly, to implantable flow connectors.

2. Related Art

The mammalian body has numerous tissue-enclosed body spaces. For example, body conduits such as blood vessels, lymph and tear ducts, bowels, urethra, etc., which have a lumen through which fluid is carried to facilitate circulation, excretion or other fluid transfer function. Tissue-enclosed body spaces also include body reservoirs such as the stomach, bladder, gall bladder, lymph nodes, etc., which temporarily or permanently retain fluid.

It is often necessary or desirable to directly or indirectly connect body spaces to one another, to other areas in the body, or to an external or implantable medical device such as a sensor, pump, drug delivery system, or other permanently or temporarily implanted therapeutic device. For example, when vessels are damaged, severed or occluded due to physiological conditions, surgical intervention, or disease, certain sections of those vessels are typically bypassed to allow for the free and continuous flow of fluids. For example, an anastomosis is commonly performed for the purpose of connecting different blood vessels together to optimize or redirect blood flow around a damaged or occluded portion of a vessel or to redirect arterial flow into the venous system for enabling dialysis access.

In the context of the peripheral vascular and/or the cardiovascular system, atherosclerosis may cause partial or complete occlusion of an arterial vessel. This may result in restricted blood flow which may compromise perfusion to the tissue served by the blood flow. In the case of an occluded coronary vessel, for example, an area of the heart's myocardium would be compromised, which may lead to a myocardial infarction or other ischemic heart syndrome such as congestive heart failure. In the case of peripheral vascular atherosclerotic disease, occluded vessels lead to ischemic syndromes such as threatened limbs, stroke and other morbidities. Many cases, such a blockage or restriction in the blood flow leading to the heart or peripheral vessels, may be treated by a surgical procedure known as an artery bypass graft procedure.

A bypass procedure involves establishing an alternate blood supply path to bypass a diseased section of a diseased or compromised artery. In the bypass procedure, a surgeon typically dissects one end of a source or 'pedicled' artery (such as the internal mammary artery in the case of coronary artery bypass), or a free vessel segment (typically the saphenous vein in the leg), to use as a graft conduit to bypass the obstruction in the affected artery to restore normal blood flow. The graft vessel is connected to the obstructed vessel by means of an anastomosis procedure wherein an opening in the graft vessel is sutured to the obstructed vessel at an arteriotomy site made within the obstructed vessel. There are other indications for vessel anastomoses including revascularizing diseased arteries by creating a side-to side anastomosis between the distal end of the artery and an adjacent vein, thereby allowing the portion of the vein distal the occlusion to become "arterialized." Another indication includes arterial revascularization by "arterializing" a vein through creation of a conduit downstream of the occlusive disease.

The creation of an arteriovenous (AV) fistula is another instance where two body conduits are joined together and involves surgically joining an artery to a vein. AV fistulas are formed for a variety of reasons, one being to provide vascular access for hemodialysis patients. In such an application, the most common site for creation of the AV fistula is the upper extremity, though the lower extremity may also be used. Various surgical techniques and methods may be employed to create the AV fistula. Another indication for creation of an AV fistula is the connection of major vessels such as the aorta and the vena cava in patients with chronic obstruction pulmonary disease (COPD).

The patency of an anastomosis contributes to a successful bypass or AV fistula, both by acute and long-term evaluation. Patency may be compromised due to technical, biomechanical or pathophysiological causes. Among the technical and biomechanical causes for compromised patency are poorly achieved anastomoses due to, for example, poor technique, trauma, thrombosis, intimal hyperplasia or adverse biological responses to the anastomosis. Improperly anastomosed vessels may lead to leakage, create thrombus and/or lead to further stenosis at the communication site, possibly requiring re-operation or further intervention. As such, forming an anastomosis is a critical procedure in bypass or AV fistula surgery, requiring precision and accuracy on the part of the surgeon.

A common traditional approach for forming an anastomosis is to suture together natural or artificial openings in the vessels. To do so, according to one approach, a surgeon delicately sews the vessels together being careful not to suture too tightly so as to tear the delicate tissue, nor to suture too loosely so as to permit leakage of fluid from the anastomosis. In addition to creating a surgical field in which it is difficult to see, leakage of fluid from the anastomosis can cause serious acute or chronic complications, which may be fatal. In addition to the inherent inconsistencies in suture tightness, incision length, placement of the suture, stitch size, and reproducibility, suturing an anastomosis can be very time consuming. This difficulty is compounded by the relatively small dimensions of the vessels involved or the diseased state of the vessel when creating an AV fistula.

SUMMARY

In accordance with one aspect of the present invention, an implantable flow connector for fluidically coupling a source tissue-enclosed body space with a destination element is disclosed, the flow connector comprising: a conduit having a lumen terminating at an orifice at a first end of the conduit implantable in the source body space through an opening formed in a tissue wall of the source body space, and a second end of the conduit implantable in the destination element through an opening in a surface of the destination element; and a circumferential flange, radially extending from the conduit proximate the conduit first end, configured to be implanted in the source body space adjacent an opening in the tissue wall of the source body space such that the conduit extends through the opening, the flange comprising one or more circumferentially adjacent sections at least one of which has a rigidity that decreases in a radially-increasing direction.

In accordance with another aspect of the present invention, an implantable flow connector for fluidically coupling a source tissue-enclosed body space with a destination element is enclosed, the flow connector comprising: a conduit having a lumen terminating at an orifice at a first end of the conduit implantable in the source body space through an opening formed in a tissue wall of the source body space, and a second end of the conduit implantable in the destination element through an opening in a surface of the destination element; and a circumferential flange, radially extending from the conduit proximate the conduit first end, configured to be implanted in the source body space adjacent an opening in the tissue wall of the source body space such that the conduit extends through the opening, the flange comprising one or more circumferentially adjacent sections constructed and arranged to reinforce the conduit.

In accordance with a further aspect of the present invention, an implantable flow connector for fluidically coupling a source tissue-enclosed body space with a destination element, the flow connector comprising: a conduit having a lumen terminating at an orifice at a first end of the conduit implantable in the source body space through an opening formed in a tissue wall of the source body space, and a second end of the conduit implantable in the destination element through an opening in a surface of the destination element; and a circumferential flange, radially extending from the conduit proximate the conduit first end, configured to be implanted in the source body space adjacent an opening in the tissue wall of the source body space such that the conduit extends through the opening, the flange comprising one or more circumferentially-opposing flange sections configured to extend around the longitudinal axis of the source body space and against the tissue wall of the source body space, and further wherein forces generated by the lateral sections being disposed against the tissue wall urge the flow connector toward the opening and against the inner surface of the tissue wall thereby causing the flow connector to be supported by the flange sections.

In accordance with a still further aspect of the present invention, an implantable flow connector for fluidically coupling a source tissue-enclosed body space with a destination element, the flow connector comprising: a conduit having a lumen terminating at an orifice at a first end of the conduit implantable in the source body space through an opening formed in a tissue wall of the source body space, and a second end of the conduit implantable in the destination element through an opening in a surface of the destination element; and a circumferential flange, radially extending from the conduit proximate the conduit first end, configured to be implanted in the source body space adjacent an opening in the tissue wall of the source body space such that the conduit extends through the opening, the flange comprising one or more circumferentially adjacent sections constructed and arranged to substantially retain the flow connector substantially in a stationary operable position within the source body space.

In accordance with another aspect of the present invention, an implantable flow connector for fluidically coupling a source tissue-enclosed body space with a destination element, the flow connector comprising: a conduit having a lumen terminating at an orifice at a first end of the conduit implantable in the source body space through an opening formed in a tissue wall of the source body space, and a second end of the conduit implantable in the destination element through an opening in a surface of the destination element; and a circumferential flange, radially extending from the conduit proximate the conduit first end, configured to be implanted in the source body space adjacent an opening in the tissue wall of the source body space such that the conduit extends through the opening, the flange comprising one or more sections each having a combination of one or more of composition and dimensions that prevents the one or more sections from substantially deflecting in response to explant forces exerted on the flow connector.

In accordance with still another aspect of the present invention, an implantable flow connector for fluidically coupling a source tissue-enclosed body space with a destination element, the flow connector comprising: a conduit having a lumen terminating at an orifice at a first end of the conduit implantable in the source body space through an opening formed in a tissue wall of the source body space, and a second end of the conduit implantable in the destination element through an opening in a surface of the destination element; and a circumferential flange, radially extending from the conduit proximate the conduit first end, configured to be implanted in the source body space adjacent an opening in the tissue wall of the source body space such that the conduit extends through the opening, wherein the flange is constructed and arranged to prevent explanation of the flow connector from the source body space in response to forces exerted on the flow connector.

In accordance with a further aspect of the present invention, an implantable flow connector for fluidically coupling a source tissue-enclosed body space with a destination element, the flow connector comprising: a conduit having a lumen terminating at an orifice at a first end of the conduit implantable in the source body space through an opening formed in a tissue wall of the source body space, and a second end of the conduit implantable in the destination element through an opening in a surface of the destination element; and a circumferential flange, radially extending from the conduit proximate the conduit first end, configured to be implanted in the source body space adjacent an opening in the tissue wall of the source body space such that the conduit extends through the opening, the flange comprising one or more sections configured to cooperate with the tissue wall to urge the flow connector out of the opening thereby causing the flange to sealingly abut the inner surface of the source body conduit.

In accordance with a still further aspect of the present invention, an implantable flow connector for fluidically coupling a source tissue-enclosed body space with a destination element, the flow connector comprising: a conduit having a lumen terminating at an orifice at a first end of the conduit implantable in the source body space through an opening formed in a tissue wall of the source body space, and a second end of the conduit implantable in the destination element through an opening in a surface of the destination element; and a circumferential flange, radially extending from the conduit proximate the conduit first end, configured to be implanted in the source body space adjacent an opening in the tissue wall of the source body space such that the conduit extends through the opening, the flange comprising one or more circumferentially-opposing flange sections, constructed with memory material and having a radius of curvature equal to or greater that the radius of curvature of the source body space, configured to conform to the inner surface of the tissue wall adjacent the opening in the body space, wherein the opposing flange sections are configured to extend around the longitudinal axis of the source body space and further wherein forces generated by said lateral sections being disposed against the tissue wall urge the flow connector out of the opening thereby causing the flange to abut the inner surface of the source body conduit.

A method for connecting a flow connector to a source and a destination tissue-enclosed body space, wherein the flow connector includes a conduit having a longitudinally-extending lumen terminating at an orifice at opposing first and second ends of the conduit, wherein a second end of the conduit is configured to be implanted in the destination element through an opening in the destination element, and a radially extending, circumferential flange proximate the first end of the conduit, configured to be implanted through an opening in a tissue wall of the source body space, comprising: coupling a second end of the conduit of the flow connector to the destination body space; temporarily reducing the size of the flange; inserting said reduced flange through the opening on the wall of said source body space; and releasing the reduced size flange thereby allowing the flange to expand from its reduced size.

BRIEF DESCRIPTION OF THE DRAWINGS

Embodiments of the present invention are described herein in conjunction with the accompanying drawings, in which:

FIG. 1A is a side view of one embodiment of a flow connector of the present invention;

FIG. 1B is a modified top view of the embodiment of the present invention illustrated in FIG. 1A taken along cross-section line 1B-1B in FIG. 1A;

FIG. 3 is a perspective view of another embodiment of the present invention illustrated with respect to a tissue-enclosed body space into which the flow connector of the present invention is to be implanted;

FIG. 10C illustrates marking an orientation line along the second tissue-enclosed body space and also forming an artificial opening on the second tissue-enclosed body space;

FIG. 10D illustrates inserting a flow connector according to one embodiment of the present invention in the second tissue-enclosed body space;

FIG. 10E illustrates a flow connector according to one embodiment of the present invention inserted and secured in a second tissue-enclosed body space with a portion of the second tissue-enclosed body space removed;

FIG. 10G illustrates a first tissue-enclosed body space after an artificial opening is manually formed;

FIG. 19 is a perspective view of one embodiment of the present invention in which an artificial conduit and two flow connectors are provided for implantation in a recipient.

DETAILED DESCRIPTION

Figure 1C:
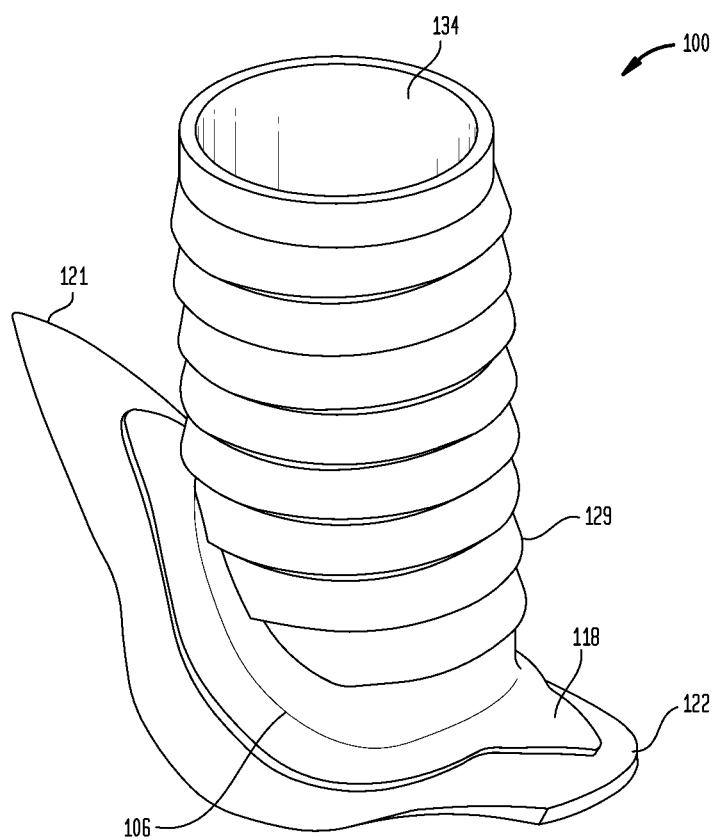
FIG. 1C is an isometric view of another embodiment of the flow connector of the present invention.

Aspects of the present invention are generally directed to an implantable flow connector, elements of an implantable flow connector and methods for manufacturing and utilizing embodiments of a flow connector. Embodiments of the flow connector of the present invention are configured to be implanted in a tissue-enclosed body space such as a body conduit or body reservoir to provide a flow path for fluid from the source body space to another body space, a man-made or body conduit, an external or implanted medical device, or other destination element.

Embodiments of the flow connector comprise a conduit having a lumen that terminates at an orifice on opposing ends of the conduit, and a flange radially extending from one of the two ends of the conduit. The flow connector is configured to be implanted into the source body space via a natural or artificial opening (e.g., a man-made opening) in a region of the tissue wall that defines the body space. The flange surrounds the conduit orifice through which the conduit lumen is fluidically coupled to the interior of the body space, and is configured to be self-retained in the body space.

The conduit is also configured to be retained in the noted destination device or body space or body region (collectively and generally referred to herein as the destination element). For example, when the destination element is a tissue-enclosed body space, the conduit is configured to be implanted into the destination body space via a natural or artificial opening in the tissue wall defining that body space. Once implanted, fluid exiting the conduit orifice at the distal end of the flow connector flows into the destination element. As such, the flow connector of the present invention fluidically couples the source body space and destination device or body space.

As noted, embodiments of the flow connector of the present invention may be used to fluidically couple any tissue-enclosed body space to any type of destination including any other tissue-enclosed body space, other areas in the body, or an external or implanted medical device. Embodiments of the flow connector may be configured to be implanted in any tissue-enclosed body space including, but not limited to, body conduits such as blood vessels, lymph ducts, tear ducts, bowels, urethra, etc., which have a lumen through which fluid is carried to facilitate circulation, excretion or other fluid transfer, as well as body reservoirs such as the stomach, bladder, gall bladder, lymph nodes, etc., which temporarily or permanently retain fluid. For ease of description, embodiments of the flow connector described below are specifically configured for implantation to create an arteriovenous (AV) fistula and, more specifically, an AV fistula in the upper or lower extremity to provide vascular access for hemodialysis patients.

FIG. 1A is a side view of one embodiment of a flow connector of the present invention. In FIG. 1A, flange 102 is a circumferential flange and is configured to radially extend from conduit 104 proximate to its first or proximal end 131 of conduit 104. Conduit 104 terminates at proximal end 131 of conduit 104 at an orifice. A second orifice is disposed on the opposite side of conduit 104 at its distal end 132. Flange 102 comprises a contact surface 126, which is configured to contact an inner surface of the tissue wall defining the source body space of a recipient when it is implanted therein. On the opposite side of flange 102 from contact surface 126 is an exposed surface 128 which is exposed to fluids passing through the source body space (not shown).

Figure 1D:
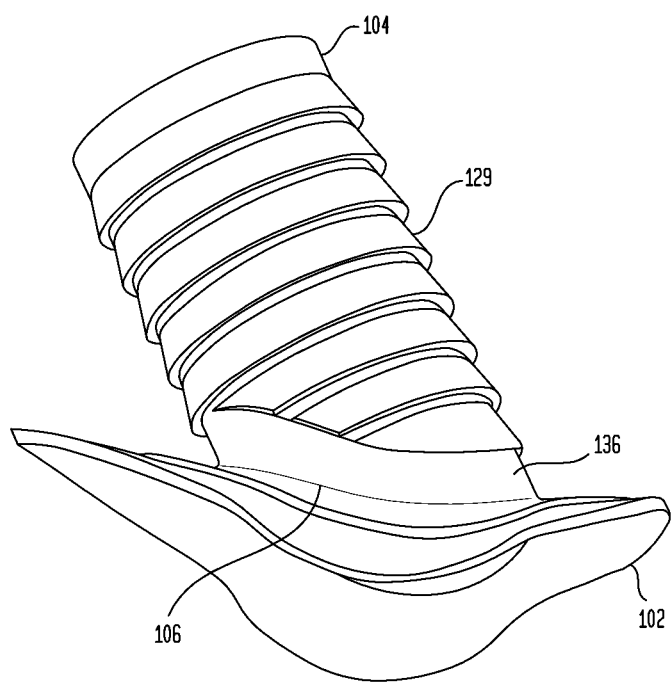
FIG. 1D is another isometric view of the embodiment of the flow connector illustrated in FIG. 1C.
Figure 1E:
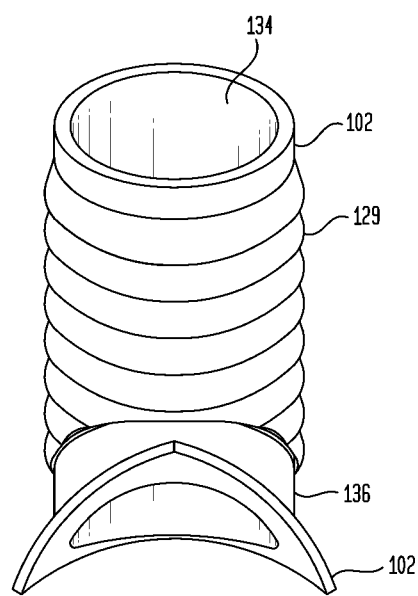
FIG. 1E is yet another isometric view of the embodiment of the flow connector illustrated in FIG. 1C.

In one embodiment of the present invention, flange 102 comprises a plurality of circumferentially adjacent sections. For example, a pair of opposing flange sections 112A and 112B. In those embodiments designed form implantation in a body conduit, flange sections 112 are referred to as longitudinal flanges, and flange section 112A is referred to as heel section 112A while flange section 112B is referred to as toe section 112B. In addition to longitudinal sections 112, there is a pair of substantially similar lateral sections 114A, 114B extending from opposing sides of conduit 104 approximately equidistant from flanges 112A, 112B. Circumferentially opposed sections 114A, 114B, also referred to herein as lateral sections 114 due to their substantially orthogonal positioning relative to longitudinal sections 112, are configured to extend from flange 102 as illustrated in FIGS. 1C-1E, on opposing sides of conduit 104, and are further configured to extend circumferentially around a longitudinal axis 110 of the source body space in which flange 102 is to be implanted. The circumferential radius of lateral sections 114A, 114B is selected based on the radius of curvature of the region of the source body space in which flow connector 100 is to be implanted. In one embodiment, the radius 297 defined from longitudinal axis 110 to contact surface 126 of lateral sections 114A, 114B is substantially equal to the radius 298 defined from longitudinal axis 110 to the inner surface of the source body space. In other embodiments, radius 297 defined from longitudinal axis 110 to contact surface 126 of lateral sections 114A, 114B is larger than the radius 298 defined from longitudinal axis 110 to the inner surface of the source body space. Furthermore, in those embodiments, flange 102 is constructed of shape-memory material such that external forces exerted on flange 102 made of memory material may cause flange 102 to at least partially bend, but the nature of the memory material will generate forces to return flange 102 to its original shape. In such embodiments where the radius of lateral sections 114A, B is greater, that radius defined from longitudinal axis 110 to contact surface 126 of lateral sections 114A, B may be 1 to 10% larger than the radius defined from longitudinal axis 110 to the inner surface of the source body space. The larger radius of lateral sections 114A, B combined with the nature of the memory material with which it is constructed will generate a chronic outward force when flow connector 100 is implanted within the source body space, which will in turn cause the walls of the source body space to resist the outward force, thereby providing a compression force to lateral sections 114A, B. The compression force applied to lateral sections 114A, B in turn urges contact surface 126 of flange 102 towards the opening in the tissue wall of the source body space, thus providing a seal between contact surface 126 of flange 102 and the tissue wall such that fluid within the source body space will not leak after implantation of flow connector 100. It is to be understood that although, in one embodiment of the present invention, some fluid from the source body space may or may not leak immediately after implantation. However, with normal physiological healing processes, such leakage will soon thereafter cease as the aforementioned seal will be provided by contact surface 126 on flange 102 with the tissue wall, thereby eliminating the need for additional elements such as glue, sutures etc. in order to stop or prevent fluid leakage.

In addition to providing a seal between contact surface 126 and flange 102, as described above, the larger radius of lateral sections 114A, B combined with the nature of the memory material with which it is constructed also acts to provide support for flow connector 100. As used herein, supporting flow connector 100 refers to physically supporting flow connector 100 such that it retains its position within the source body space, after implantation, without other components or objects contributing towards the retaining of its implanted position.

In one embodiment of the present invention, lateral sections 114A, B extend circumferentially around the interior surface of the source body space so as to leave approximately 180° of the source conduit's interior surface circumferentially uncovered by lateral sections 114A, B and flow connector 100 generally. By leaving approximately 180° uncovered, obstruction to the flow of fluid within the source body space is minimized while enhancing stability provided by lateral sections 114A, B to flow connector 100 when implanted. Longitudinal sections 112 are also circumferentially curved with respect to the interior surface of the source body space such that contact surface 126 makes contact with the interior surface of the source body space in a sealing region 116, thereby providing a hydrophobic seal as well as stability between flow connector 100 and the source body space.

Adjacent to sealing region 116 is reinforcement region 118, configured to provide physical support to flow connector 100 by being constructed and arranged to oppose various explanting or other forces that may be exerted on flange 102 and conduit 104 when flow connector 100 is implanted in the source body conduit. Reinforcement region 118 is configured to have a rigidity that it aids in the opposition of deflection forces, and is therefore less prone to flexing of portions of flange 102 and/or conduit 104. The rigidity of reinforcement region 118 decreases in a radially-increasing direction thereby aiding in the implantation of flange 102 in the source body space. It should be appreciated that the rigidity may be provided in various ways, according to various embodiments of the present invention. For example, reinforcement region 118 may have a composition with a rigidity which makes it more rigid than sealing region 116 or other portions of flange 102. For example, in one embodiment of the present invention, sealing region 116 may be manufactured with material having a Shore value of 80A and reinforcement region 118 may be manufactured with material having a Shore value of 55D. In other embodiments, reinforcement region 118 may be manufactured with the same material as its adjacent or other sections of flange 102, but reinforcement region 118 may be configured to be thicker than adjacent sections of flange 102, thereby making reinforcement region 118 more rigid. By avoiding substantial deflecting or bending, flange 102 remains larger than the aperture in the source body space through which flange 102 was inserted, thus preventing explanting or pull-out from the source body space. As used herein, substantial deflecting by flange 102 refers to the reduction of the surface area of flange 102 to a size allowing flange 102 in its deflected state to fit through aperture in the source body space through which flange 102 was inserted.

Reinforcement region 118 is proximal to conduit 104 so as to provide structural integrity to conduit 104 such at the orifice at the proximal end 131 of conduit 104 can withstand a greater amount of compression force than without reinforcement region 118 being present. As will be further discussed below, reinforcement region 118 also may assist in opposing explant forces that may be applied, intentionally or inadvertently, on flow connector 100. Although reinforcement section 118 is illustrated in FIGS. 1A-1C to be substantially contiguous, it is to be understood that in other embodiments of the present invention reinforcement section 118 may not be contiguous but may have multiple reinforcement regions 118 disposed circumferentially around conduit 104. Similarly, it is to be understood that although reinforcement region 118 is illustrated in FIG. 1B is shown as having a similar or at least a corresponding perimeter as that of flange sections 112, 114, in other embodiments of the present invention, reinforcement region 118 may have a perimeter which is shaped differently from that of flange sections 112, 114.

Longitudinal sections 112 are configured to facilitate implantation of flow connector 100 while also opposing pull-out forces which may otherwise pull flow connector 100 out from the source body space (not shown) after flow connector 100 is implanted. Lateral sections 114A, B are also configured to facilitate implantation and further configured to maintain the position of flow connector 100 with respect to the source body space (not shown) after flow connector 100 is implanted. In one embodiment of the present invention, lateral sections 114A, B have a radius of curvature substantially identical to the radius of curvature of the source body space into which it is to be implanted. In other embodiments of the present invention, lateral sections 114A, B has a curvature radius which is slightly larger than the curvature radius of the source body space into which it is to be implanted. When this embodiment is implanted in the source body space, the larger curvature radius of lateral sections 114A, B will cause the source body space to generate compression forces on the larger lateral sections 114A, B which will in turn promote the maintenance of the position of flow connector 100 in the source body space.

FIG. 1B is a cross-sectional view along the line 1B-1B noted in FIG. 1A, in which a substantial portion of the conduit body 130 is shown as if removed for the purpose of showing an unobstructed view of the longitudinal sections 112 and lateral sections 114. In the embodiment shown in FIG. 1B, heel section 112A and toe section 112B have apices, heel section apex 121 and toe section apex 122, respectively, when viewed from the perspective illustrated in FIG. 1B. In this embodiment, heel section apex 121 and toe section apex 122 come to a sharp point which may be helpful in redirecting fluid flowing within the source body space so as to prevent or minimize disturbances in flow shear stress, eddy flow, foil effects, turbulence, resistance, tube wall deformation, and tensile stress/strain distributions that can lead to intimal hyperplasia and other similar or associated conditions. Similarly, as depicted in FIG. 1A, flange edge 140 may be chamfered to an angle, for example 60°, so as to similarly redirect fluid flowing within the source body space for the same purpose.

Multiple cutout regions 124 are disposed between longitudinal sections 112 and lateral sections 114. Cutout regions 124 represent an absence of material between those flanges 112, 114 and are dimensioned and configured to facilitate temporary foldover of flanges 112, 114 during implantation of flow connector 100. Sealing region 116 is also disposed over a portion of cutout regions 124 to ensure that the contact surface 126 around conduit body 130 is sealed with respect to the source body space so that fluids flowing through the source body space remains either within the source body space or through the lumen of conduit 104.

Figure 1F:
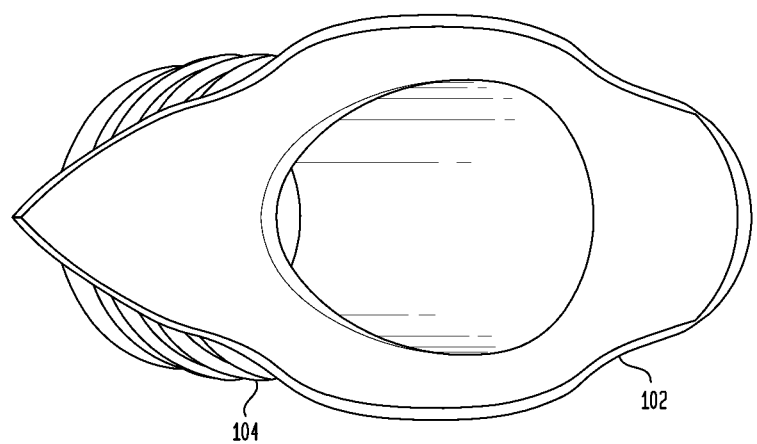
FIG. 1F is a further isometric view of the embodiment of the flow connector illustrated in FIG. 1C.

As noted above, flow connector 100 also comprises conduit 104 which is connected to flange 102 along joint region 106. At joint region 106, the proximal end 131 of conduit body 130 and flange 102 are joined such that first conduit orifice 120 leads into the lumen of conduit body 130, as illustrated in FIGS. 1E and 1F, which shows at least a partial view of exposed surface 128 of flange 102, as well as first conduit orifice 120 leading into the lumen of conduit body 130. In the embodiment illustrated in FIGS. 1A and 1B, conduit portion 106 is depicted largely as comprising a cylindrical conduit body 130. However, it is to be appreciated by one having ordinary skill in the art that conduit body 130 may have other shaped tubular bodies other than a cylindrical one in other embodiments of the present invention. For example, in other embodiments of the present invention, conduit body 130 may comprise a conduit body 130 with a rectangular or irregular cross section and a similarly shaped longitudinal lumen disposed therein. On the opposite end of conduit body 130 from proximal end 131 is distal end 132 of conduit body 130 as well as second conduit orifice 134 which is disposed at distal end 132. Second conduit orifice 134 allows fluid flow traveling through the lumen of conduit body 130 to exit through second conduit orifice 134. For example, in one embodiment of the present invention in which a source body space, such as a vein or artery, is coupled to conduit 104, fluid flowing through the source body space into which flange 102 is implanted is diverted through first conduit orifice 120, through the lumen of conduit body 130 and out of second conduit orifice 134 into the source body space.

Although the construction of flow connector 100 may vary depending on the one or more source conduits in which flow connector 100 is to be implanted, embodiments of the present invention may differ in terms of the material comprising flow connector 100, the durometer values of materials selected, thicknesses of the various components of flow connector 100 described herein or shown in the figures, and are considered a part of certain embodiments of the present invention. In one embodiment, flange 102 has a thickness ranging between approximately 0.15 mm and approximately 0.35 mm. Similarly, the outside diameter of conduit body 130 has a similar thickness range between approximately 0.15 mm and 0.50 mm and more preferably, of between approximately 0.30 mm and approximately 0.45 mm. In another embodiment, the outside diameter of conduit body 130 has a thickness of approximately 0.35 mm. The thickness of flange 102 may be decreased as flange 102 is made to extend further which will maintain the pullout forces necessary for flange 100 to be pulled out of the source body space in which it is implanted. Similarly, the thickness of flange 102 may be increased as the flange 102 is made to extend less.

Figure 5:
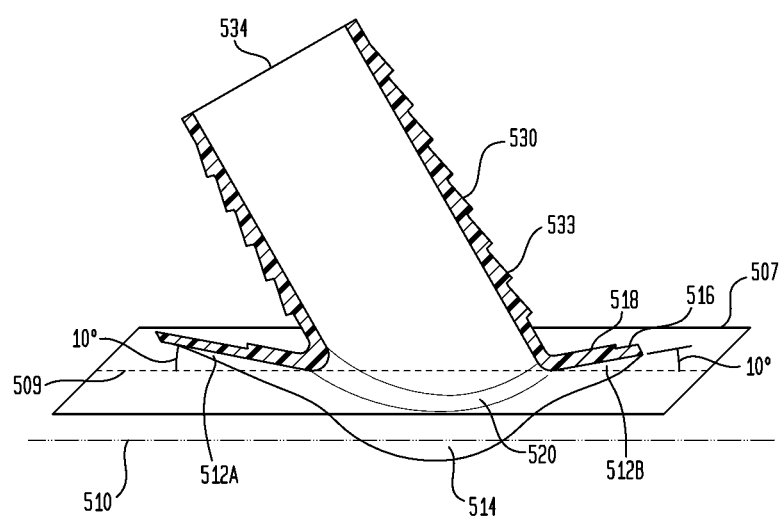
FIG. 5 is a cross-sectional view of one embodiment of the present invention with an imaginary plane having an imaginary midline.

As shown in FIG. 1C-1F and in cross-section in FIG. 5, conduit body 130 may comprise a series of barbs or protrusions 129 which extend radially from conduit body 130. In one embodiment of the present invention, the protrusions 129 provide periodic increases in the outside diameter of conduit body 130 so that the source body space within which conduit body 130 is inserted are positioned over conduit body 130 in a friction fit over the increased diameter portions of protrusions 131. Furthermore, once the source body space is positioned over conduit 104 over protrusions 131, one or more sutures may be disposed circumferentially around conduit body 130 and in the areas between conduit body 130 and the outer diameter of protrusions 131, thereby snugly retaining the source body space in place with respect to conduit 104. When one or more sutures are thus disposed, the one or more sutures that compress the source body space towards the conduit portion 104 will maintain its position since the diameter of the one or more sutures are fixed to be smaller than the outer diameter of the protrusions, which therefore provides an interference fit to prevent the one or more sutures from translating along the longitudinal axis 108 of conduit body 130.

Figure 2A:
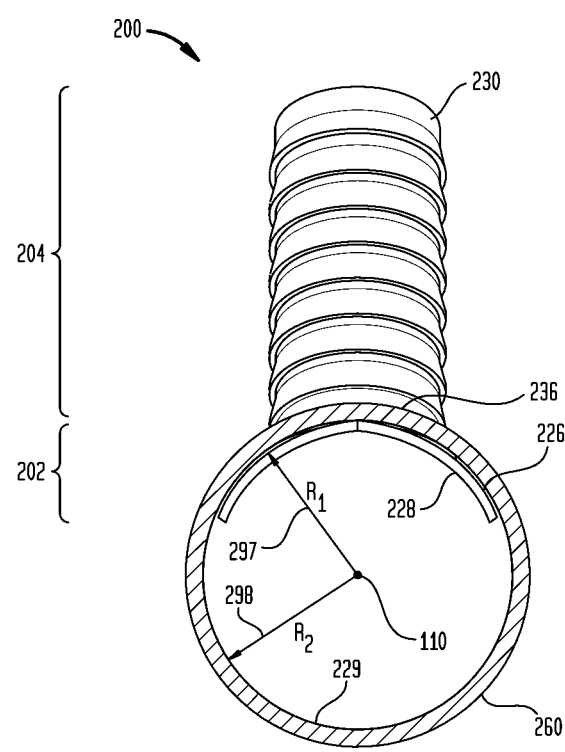
FIG. 2A is a cross-sectional view of a first tissue-enclosed body space in a recipient having one embodiment of the present invention implanted therein.
Figure 2B:
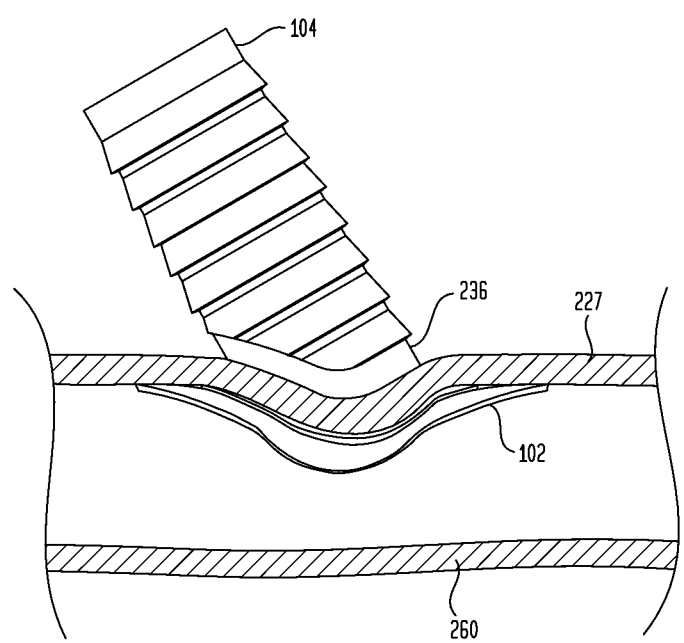
FIG. 2B is another cross-sectional view of a first tissue-enclosed body space in a recipient having one embodiment of the present invention implanted therein.

In certain embodiments of the present invention, conduit body 130, shown in FIGS. 2A and 2B as conduit body 230, has a conduit recess 236 disposed thereon. Conduit recess 236 is configured such that a source body space, such as source body space 260, rests within conduit recess 236 when flange 102, shown in FIGS. 2A and 2B as flange 202, is positioned within the source body space as described below. In one embodiment of the present invention, conduit recess 236 is configured to have a depth of between 0.5 mm and 1.0 mm in order to accommodate a source body space to allow it to rest therein. In other embodiments of the present invention, recess 236 may be configured to have a deeper recess, for example 1.0 mm. The height of the conduit recess 236, measured from flange 202 toward the distal end of conduit body 204 is approximately 0.8 mm, which will vary depending on the thickness of the source body space 260 which is accommodated within conduit recess 236, as depicted in FIG. 2A. Also as shown in FIG. 2B, conduit 204 of one embodiment of the present invention is shown to be angled approximately 60° from the horizontal axis in the illustration with respect to flange 202. This angle may vary in other embodiments of the present invention depending on the situation or the needs of the recipient. For example, in other embodiments of the present invention, conduit 204 may be configured with an angle between 10° to 90° from the horizontal axis shown in FIG. 2B. As one having skill in the art would appreciate, this angle can be from the opposite side as well with respect to flange 202.

As noted previously, flow connector 100, shown in FIG. 3 as flow connector 300, is configured to be at least partially placed within a source body space. In the embodiment illustrated in FIG. 3, flange 102 is configured to be positioned through an opening 303 on source body space 360. More specifically, one or more of heel section 312A, toe section 312B, and lateral sections 314A, B are temporarily deformed or bent with respect to flow connector 100 so that flange 102 can be inserted through opening 303. Opening 303 may be an existing opening or may be manually and/or intentionally formed, at least in part, to allow flange 102 to be inserted therethrough during the implantation of flow connector 300 within source body space 360. In the embodiment shown in FIG. 3, heel section 312A is longer than toe section 312B. The greater length of heel section 312A is configured to promote stability and the position of flange 102 within source body space 360. Additionally, the shorter length of toe section 312B, in the present embodiment of the invention, is configured to promote easier insertion of flange 102, especially in implantation methods where only lateral sections 314A, B are temporarily deformed, with longitudinal sections 312 inserted through opening 303 in their substantially extended position.

In the embodiment illustrated in FIG. 3, the fluid flowing substantially along longitudinal axis 310 through source body space 360 is flowing from the direction of heel section 312A and flowing towards the direction of toe section 312B. As is seen in the embodiment illustrated in FIGS. 1 and 3, the longitudinal axis 108 of conduit body 130 is angled with respect to the longitudinal axis 310 of source body space 360 at an angle of approximately 60° towards to direction of heel section 312A. In this embodiment of the present invention, the 60° angled source body space 360 is provided to promote, among other things, a controlled rate and/or volume of fluid flow from source body space 360 into conduit body 330. In other embodiments of the present invention, that angle may not be 60°, but may instead be some other angle, depending on the placement of flow connector 300 within the recipient or the purpose for which flow connector 300 will be used once implanted. For example, in other embodiments of the present invention, conduit body 330 may be angled 90 or 120° with respect to longitudinal axis 310 in order to achieve a desired rate or volume of flow from source body space 360.

Figure 4:
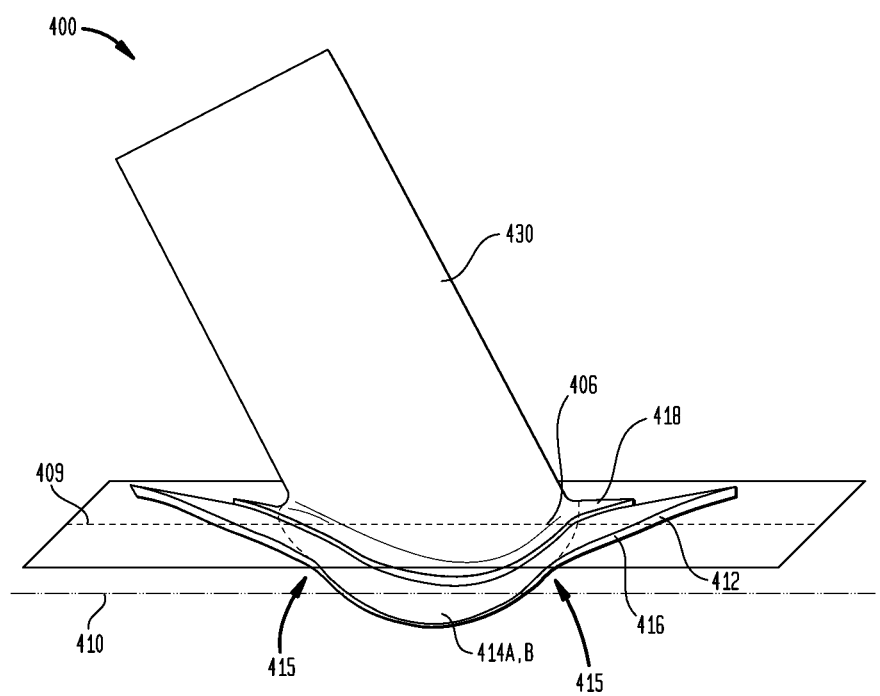
FIG. 4 is a perspective view of one embodiment of the present invention with an imaginary plane having an imaginary midline.

In FIGS. 4 and 5, an imaginary plane having a midline 409 is shown with respect to flow connector 400 and longitudinal axis 410 of source body space (not shown), according to one embodiment of the present invention. Midline 409 is parallel with respect to longitudinal axis 410 and is disposed on the exposed surface 128 around first conduit orifice 120. In the embodiment depicted, longitudinal sections 412 are angled upwards 10° from midline 409 starting at transition points 415 as shown. In other embodiments of the present invention, longitudinal sections 412 may be angled by a different amount, for example between 0 and 15°. The angling of longitudinal sections 412 upwards towards the inner surface of the source body space in which flow connector 400 is implanted will cause to be generated one or more deflection forces as a result of longitudinal sections 412 being pressed into the wall of the source body space. These deflection forces will cause a deflection of longitudinal sections 412 downward such that longitudinal sections 412 will be more parallel with midline 409 and longitudinal axis 410 of the source body space. This deflection downward will permit later flanges 414A, B to be disposed closer to the inner wall of the source body space than if the deflection did not occur, and will also cause a broader contact between contact surface 126 and the inside wall of the source body space once flow connector 400 is positioned within the source body space. FIG. 5 illustrates the imaginary lane with midline 409, now shown as midline 509, as well as the 10° angling of longitudinal sections 412, now shown as longitudinal sections 512, with respect to longitudinal axis 510 of the source body space.

Figure 6:
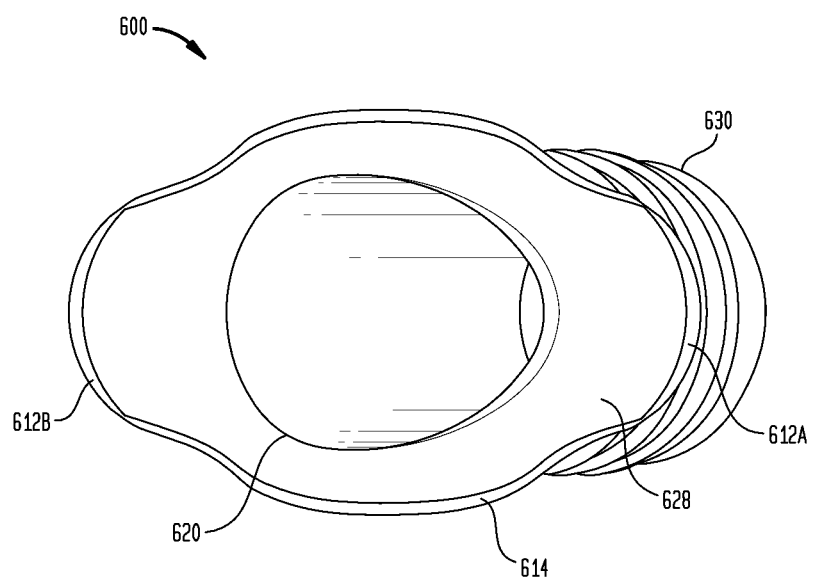
FIG. 6 illustrates a bottom view of another embodiment of the flow connector of the present invention.

Embodiments of the present invention include embodiments having different configurations of longitudinal and lateral sections. In the embodiment illustrated in FIG. 6, longitudinal sections 612A and 612B have about the same dimensions. In FIG. 6, heel section 612A is configured to be longer and to come to a pointed apex as illustrated. Toe section 612B is configured to be shorter than heel section 612A and has an apex which is more round than the apex of the heel section 612A. The shorter length of toe section 612B is sufficient, in cooperation with longer heel section 612A, to oppose the pullout forces described previously, while promoting easier insertion of flange 602 into the opening (not shown) of the source body space. In certain embodiments of the present invention, sections 612A, B are configured to each be approximately 35-65% in length of the outside diameter of first conduit orifice 620. In alternative embodiments of the present invention, sections 612A, B are each configured to be approximately 50% in length of the outside diameter of first conduit orifice 620

Figure 7A:
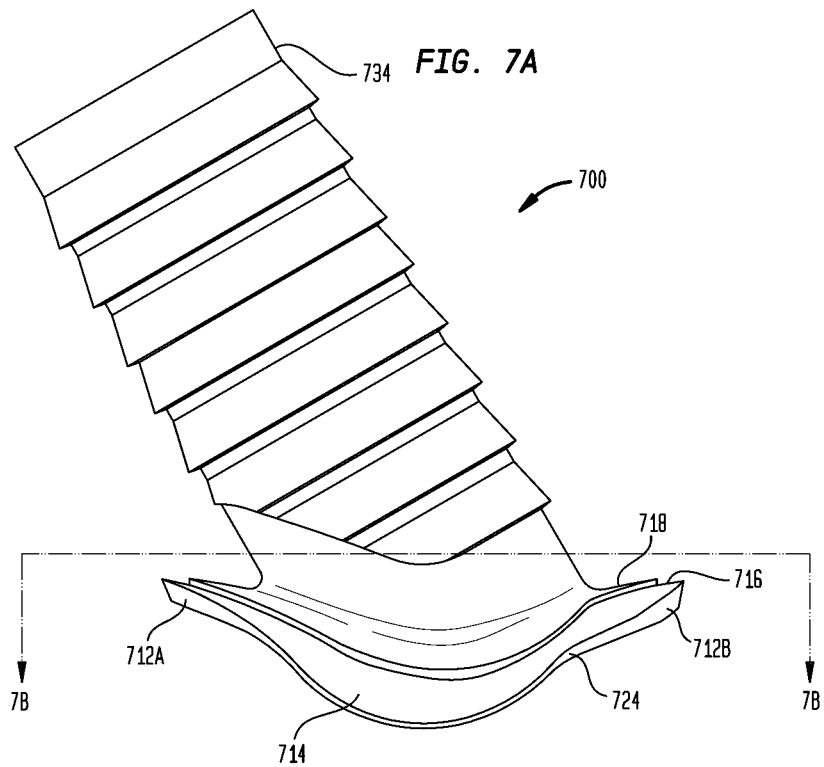
FIG. 7A illustrates a perspective view of one embodiment of the present invention having shorter longitudinal sections than the embodiment illustrated in FIG. 1A.
Figure 7B:
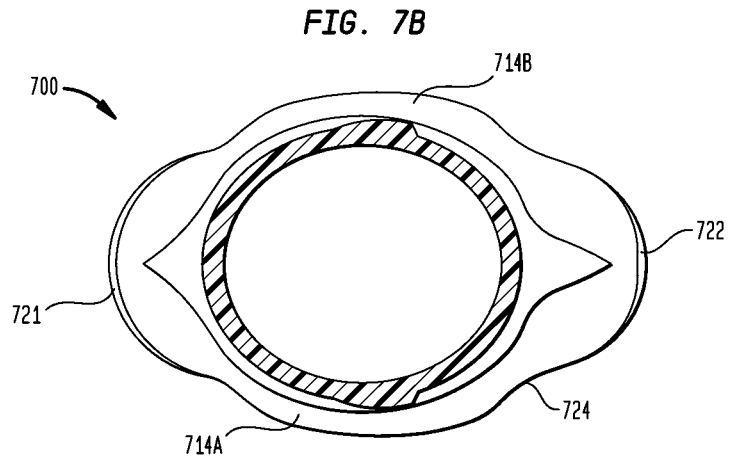
FIG. 7B illustrates a perspective top view of the embodiment illustrated in FIG. 7A.

Similarly, in the embodiment illustrated in FIGS. 7A and 7B, longitudinal sections 712 are configured substantially identically to one another. As shown, heel sections 712A and toe section 712B are both shorter than in other embodiments shown and described herein. FIG. 7B is a view along cross-section line 7B-7B and shows conduit body 730 as if it were partially removed from flow connector 700. The embodiment of the present invention illustrated in FIGS. 7A and 7B is appropriately configured and dimensioned so as to maintain the compensation for pullout forces by longitudinal and lateral sections 712 and 714, respectively. As noted previously, the thickness of sealing region 116 and reinforcement 118 may of flanges 712, 714 may be increased in order to provide make flanges 712, 714 more rigid. Alternatively, in other embodiments of the present invention, those components may be constructed of a more rigid material. FIGS. 7A and 7B also depicts cutout regions 724 which at least partly promotes flexibility of flanges 712, 714 as one or more of flanges 712, 714 are temporarily brought together during implantation of flow connector into the recipient's source body space.

Figure 8A:
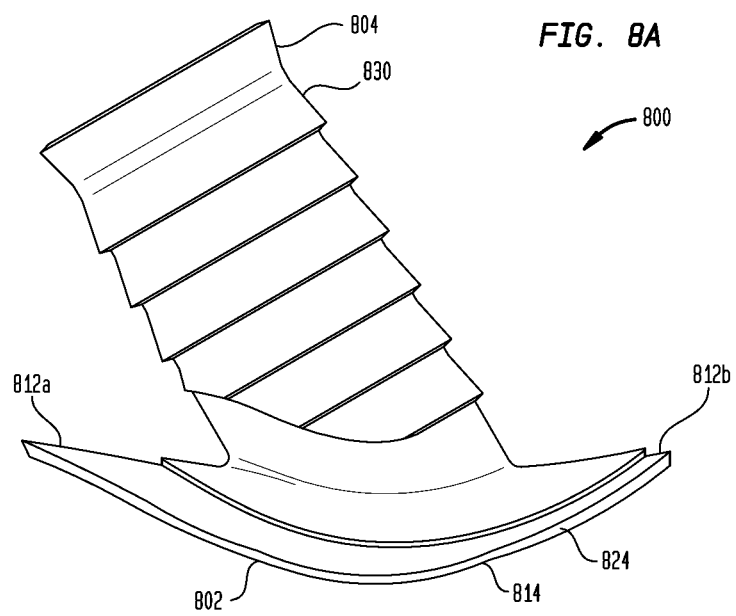
FIG. 8A is a simplified side of another embodiment of the present invention.
Figure 8B:
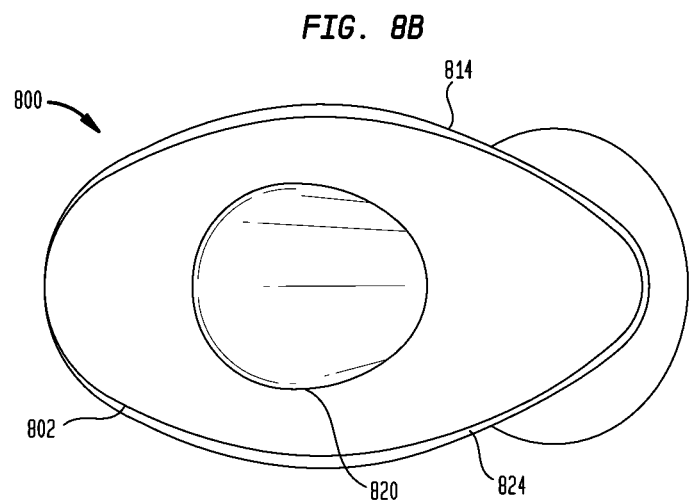
FIG. 8B is a simplified bottom view of another embodiment of the present invention.

FIGS. 8A and 8B illustrates yet another embodiment of the present invention in which cutout region 824 has zero to little reduction in the material which comprises the flange 802 of flow connector 800. Flange 802 may be constructed and dimensioned to be readily bendable upon receiving an external force, such as from a pickup tool being operated by a surgeon, despite having a very minimal or no absence of material in the cutout region 824. It should be understood by persons having skill in the art that cutout region 824, and other parts of flange 802 and conduit portion 804 may be modified before or during the implantation procedure, as will be further discussed below. Therefore, cutout region 824, or longitudinal sections 812 and lateral sections 814 may be modified in vivo to accommodate the dimensions of the source body space or the opening through which flange 802 is to be inserted during implantation of flow connector 800.

Figure 9A:
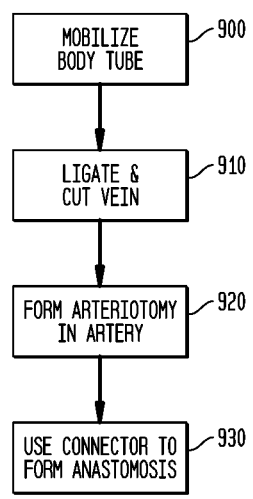
FIG. 9A is a high level flowchart of a method for implanting a flow connector according to one embodiment of the present invention.
Figure 9B:
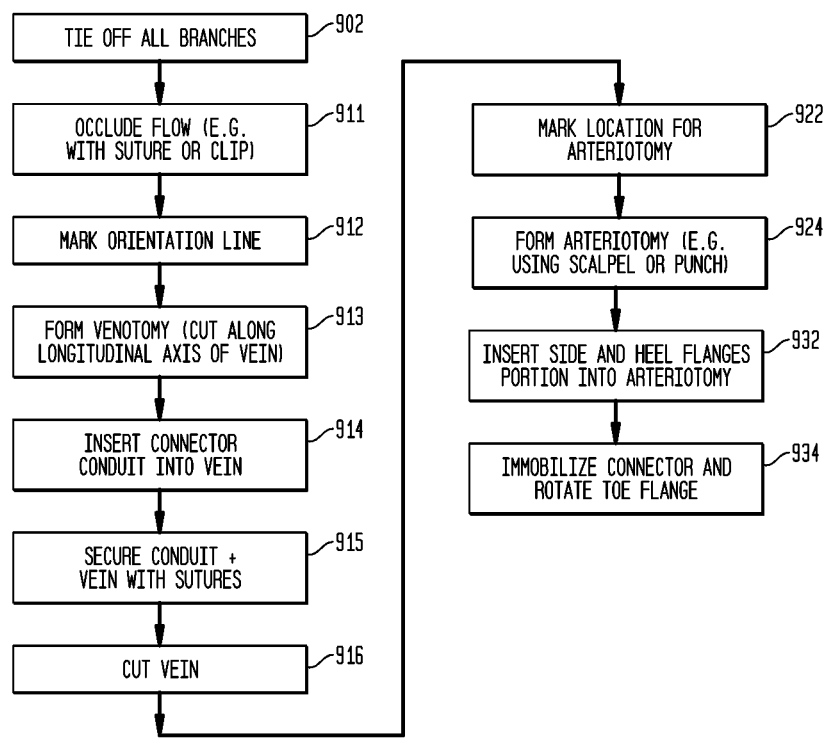
FIG. 9B is a detailed flowchart of one method for implanting the flow connector of the present invention, in accordance with one embodiment of the present invention.

In operation, embodiments of the present invention may be implanted in numerous ways. In one particular method of operation as depicted in FIG. 9A, the source body space is mobilized 900 from other conduits fluidically coupled to the destination body space. The destination body space, for example a vein of a recipient, is ligated and then cut 910 to receive the conduit 104 of flow connector 100. Once the destination body space has conduit 104 fitted therein, an opening is formed 920 in the source body space. Flange 102 of the flow connector, having the destination body space coupled thereto, is inserted through the formed opening in order to join 930 the source and destination body spaces together.

Figure 10A:
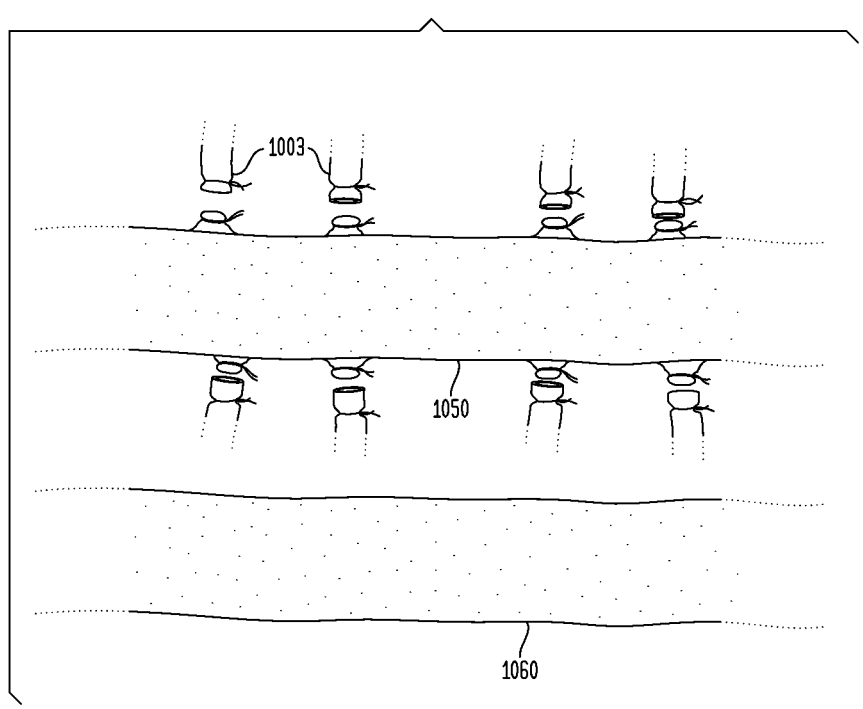
FIG. 10A illustrates tying off all branches from the second tissue-enclosed body space, according to one embodiment of the present invention.
Figure 10B:
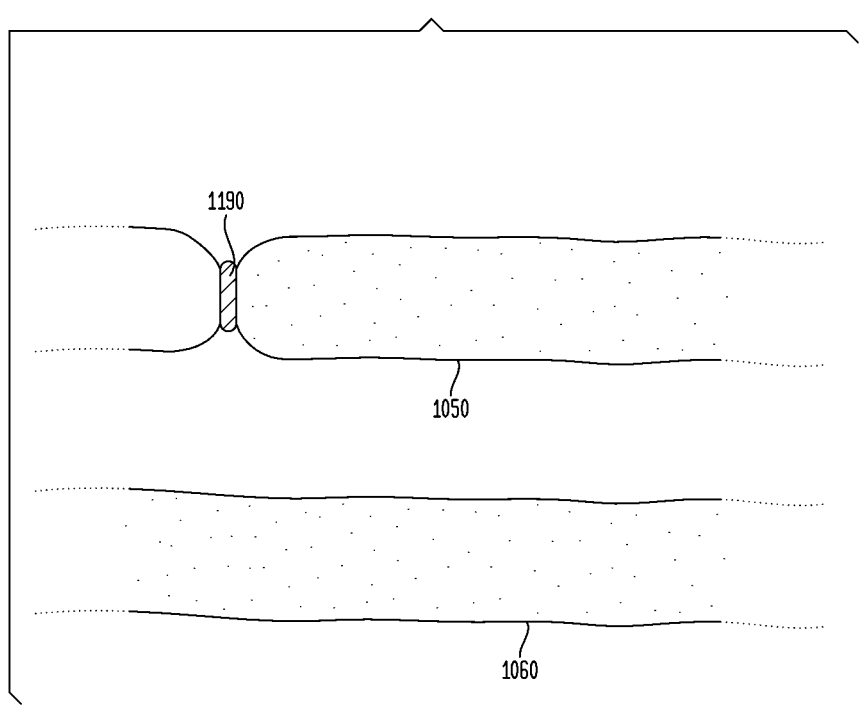
FIG. 10B illustrates occluding flow of liquids within the second tissue-enclosed body space.
Figure 10F:
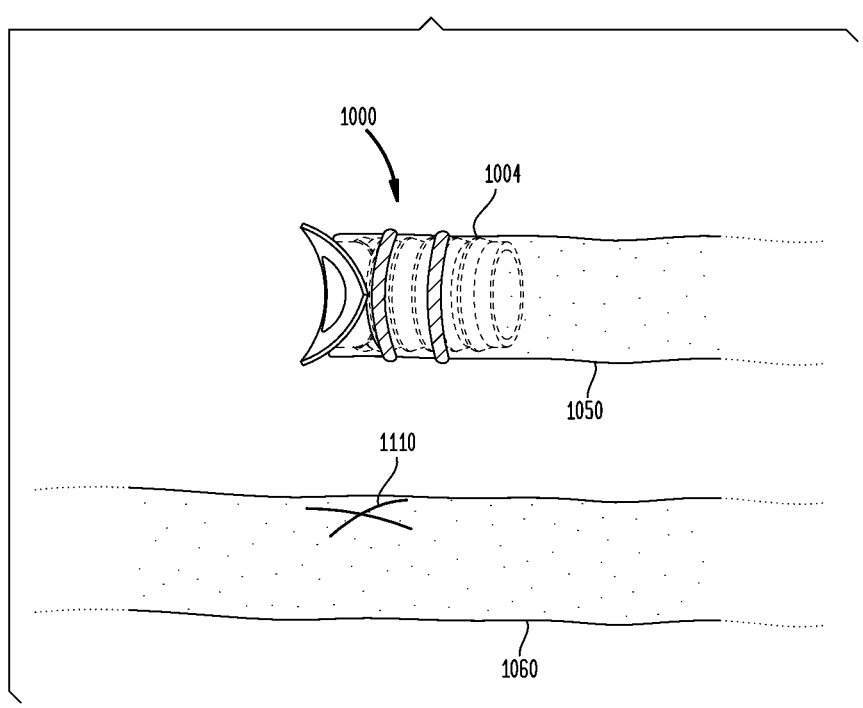
FIG. 10F illustrates marking a position on the first tissue-enclosed body space where an opening will be formed.

Expanding on the method outlined above and as further shown in FIG. 9B and FIGS. 10A-10H generally, according one embodiment of the present invention, all branches 1003 of other conduits within the body of the recipient are severed or otherwise fluidically decoupled or tied-off 902 from destination body space 1050, as illustrated in FIG. 10A. As shown in FIG. 10B, destination body space 1050 itself is then tied-off or otherwise occluded 911 using a tie or suture 1100. FIG. 10C shows that an orientation line 1102 line is marked on destination body space 1050, and an opening 1104 is formed along orientation line 1102. As illustrated in FIG. 10D, conduit portion 102 of flow connector 1000 is inserted 914 through opening 1104. FIG. 10E illustrates two sutures 1006 which are secured onto destination body space 1050 prior to the occluded end being cut away 916 from the destination body space portion now having flow connector 1000 secured thereto. In FIG. 10F, a location is identified and marked 922 where an opening in source body space 1060 is to be formed. Once an opening 1112 is formed 924, as shown in FIG. 10G, flange 1002 of flow connector 1000 is inserted through opening 1112 and permitted to be securely retained the walls of source body space 1060 in cooperation with lateral sections 114 and longitudinal sections 112.

Figure 14:
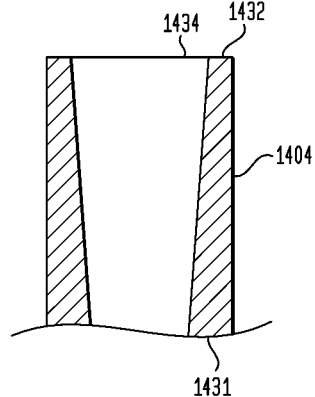
FIG. 14 is a cross-sectional view of a second interface according to yet another embodiment of the present invention in which the outer diameter remains substantially constant while the wall thickness decreases towards.

A cross-section of a portion of conduit 1404 according to one embodiment of the present invention is illustrated in FIG. 14. In FIG. 14, the portion shown illustrates a ramp configured to improve the flow from proximal end 1432 to distal end 1432 and out conduit orifice 1434 as it enters the destination element (not shown), for example a blood vessel. In FIG. 14, for the portion illustrated, the inside diameter of conduit 1404 gradually increases while the outside diameter of conduit 1404 remains substantially unchanged. By making the inside diameter of conduit 1404 substantially equal to the inside diameter of the destination element, the flow can across the cross-section of orifice 1434 is as uniform or consistent as possible, thus minimizing turbulence and other disturbances in flow which can lead to undesirable biological responses such as intimal hyperplasia. It will be understood that the ramp feature may be provided at either end of conduit 1404, to provide a smooth flow into and/or out of conduit 1404. For example, in one embodiment of the present invention, a ramp feature is disposed at both ends of conduit 1404 and promotes a smooth inflow of fluid into conduit 1404 for a limited length of conduit 1404, followed by a length of conduit 1404 in which the inside diameter remains constant, followed by a final distal length of conduit 1404 wherein a ramp having a gradually increasing inside diameter is provide and facilitates a non-turbulent outflow of the fluid out of conduit orifice 1434.

In other embodiments of the present invention, the outside diameter of conduit 1404 may change from the proximal end 1431 to distal end 1432. For example, in one embodiment, the outside diameter at each end may decrease gradually along its length. In another embodiment of the present invention, the outside diameter may increase gradually along its length. In yet further embodiments, the outside diameter may increase for some length, before decreasing for another length, and vice versa. As one having ordinary skill in the art will recognize, the outside diameter may be adjusted to be constantly or variably changing to meet specific needs or for specific uses.

In certain embodiments of the present invention, the second end of conduit 104 is configured to have an inside diameter approximately equal to the inside diameter of the destination element's lumen, for example the lumen in a blood vessel. As discussed previously, matching the inside diameters of the distal end of conduit 104 and the destination element at the point in each where fluid flow transitions from one to the other significantly reduces eddy current flow and other disturbances in the flow, which in turn reduces the occurrence of clots, thrombus, intimal hyperplasia, and other conditions which are largely undesirable. In other words, these features enable embodiments of the flow connector of the present invention to restore anatomical blood flow; that is, laminar flow, which is the normal condition for blood flow throughout most of the circulatory system. As one of ordinary skill in the art would appreciate, laminar flow is characterized by concentric layers of blood moving in parallel down the length of a blood vessel. In other words, the highest velocity is found in the center of the vessel while the lowest velocity is found along the vessel wall.

Other types of flow disturbances may include, but are not limited to, dead flow areas where a swirling or other types of flow pattern which deviates from a generally linear flow are formed by too steep of a step or diameter change with respect to certain factors such as the rate of flow, the viscosity of the fluid, the inside diameters of conduit 104 and the destination element, among others. In one embodiment of the present invention, conduit 104 has a chamfered distal end 132 or a gradually tapering distal end 132 in which the inside diameter gradually increases approaching the opening of the destination conduit. In another embodiment of the present invention, conduit 104 terminates at orifice 134 proximal the destination conduit at a knife-edge, where the wall thickness immediately proximal to the destination element approaches zero.

As illustrated in FIGS. 1F and 13-15, the inside surface of conduit 104 (also 1304, 1404, 1504), is a substantially frictionless surface configured to allow fluid flow over the surface without undergoing friction. This smooth surface minimizes or eliminates turbulence which might otherwise be generated during the flow through conduit 104.

Figure 10H:
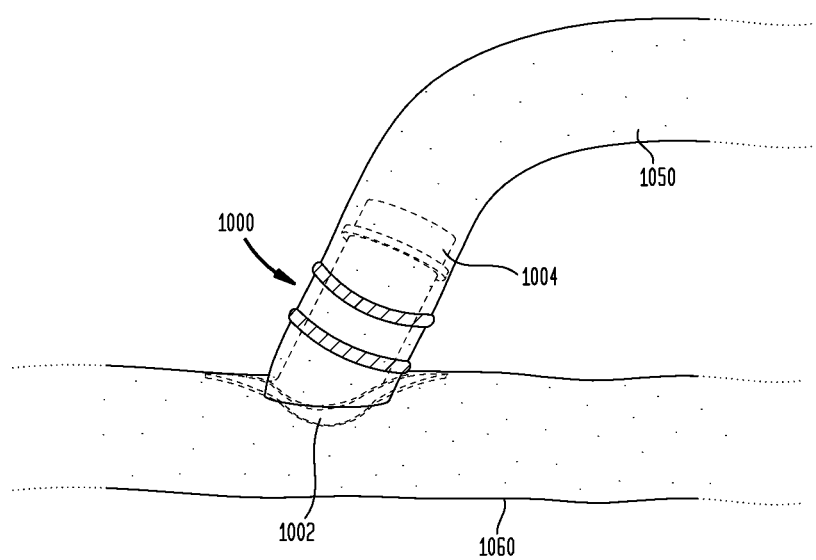
FIG. 10H illustrates a first tissue-enclosed body space connected to a second tissue-enclosed body space via one embodiment of the present invention.
Figure 12A:
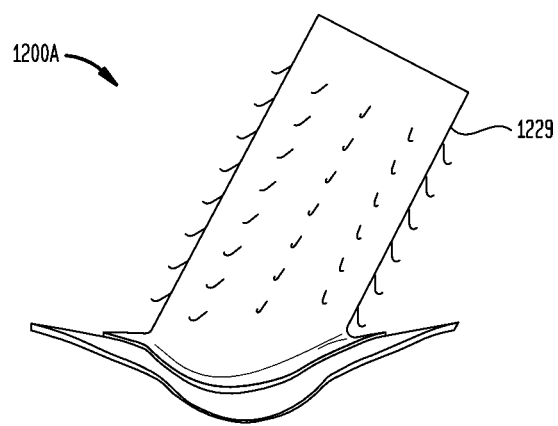
FIG. 12A illustrates another embodiment of the present invention in which the second interface further comprises barbs.
Figure 12B:
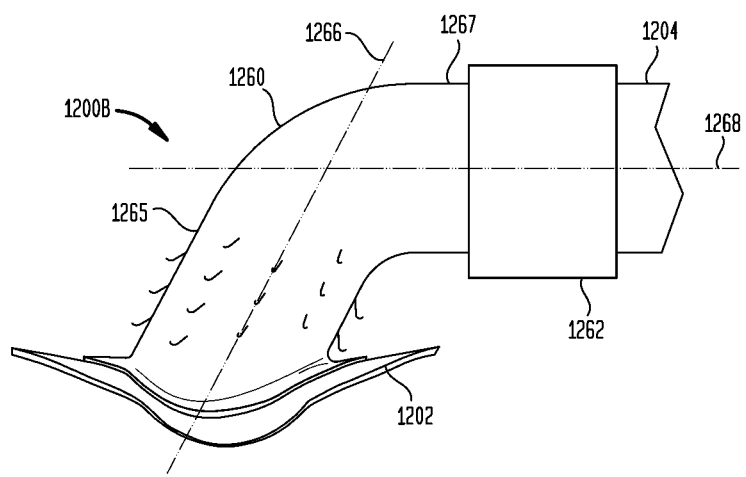
FIG. 12B illustrates yet another embodiment of the present invention in which the second interface comprises an elbow as well as a retention collar.

FIG. 12B illustrates another embodiment of the present invention in which bend 1260 is provided at a point along conduit 1204. The internal surface of bend 1260 in conduit 1204 redirects fluid flowing through conduit 1204, from flange 1202 to the destination elements, for example a blood vessel. In the embodiment illustrated in FIG. 12B, a first pre-bend longitudinal axis 1266 is shown as well as a second post-bend longitudinal axis 1268. In the illustrated embodiment, fluid flowing from flange 1202 through a first pre-bend portion 1265 is redirected by bend 1260 before the fluid enters a second post-bend portion 1267. While the fluid is thus redirected, conduit 1204 at bend 1260 absorbs the force from the fluid flowing towards bend 1260 as it is redirected towards the destination element (not shown), thus avoiding those forces being applied to a body vessel which would otherwise have received the forces. Using embodiments of the present invention having one or more bends 1260 as described, it is possible to provide an improved connection between the source body space and the destination element. For example, where the source body space is a artery and the destination element is a vein, as illustrated according to a different embodiment of the present invention in FIGS. 10A-10H, flow connector 1200B may be utilized to connect body space or vein 1050 with body space or artery 1060 but such that vein 1050 need not be bent as shown in FIG. 10H. Instead, connector 1200B is configured with a bend 1260 which would extend from artery 1060 and then bend towards the opening in vein 1050 such that vein 1050 remains substantially straight.

Figure 15:
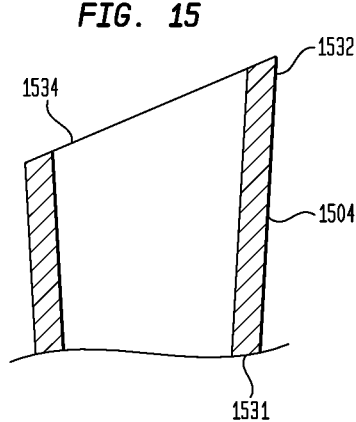
FIG. 15 is a cross-sectional view of a second interface according to yet another embodiment of the present invention in which the distal end of the second interface is uneven.
Figure 16:
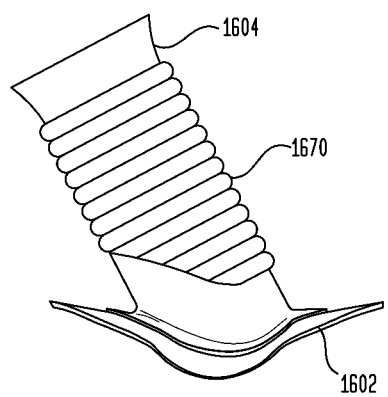
FIG. 16 illustrates an embodiment according to the present invention in which the first interface and second interface are formed separately and then joined together before implantation.

In further embodiments of the present invention, as illustrated in FIG. 15, distal end 1532 of conduit 1504 is beveled such that orifice 1534 at distal end 1532 is not 90° with respect to the longitudinal axis of conduit 1504. In the embodiment illustrated, the beveled distal end 1532 is approximately 30° from a plane orthogonal to the longitudinal axis of conduit 1504. However, a person having ordinary skill in the art will appreciate that the angle may be different depending on the situation in which an embodiment of the present invention is to be used. Beveled distal end 1532 facilitates a better transition of fluid flowing through conduit 1504 and exiting at beveled distal end 1532 into the destination element by accommodating a bend in the destination element by allowing an earlier exit of the fluid flow in the direction of the bend in conduit 1504. For example, the embodiment illustrated in FIG. 15 has a beveled end 1532 such that orifice 1534 is biased towards the left. This left-facing orifice 1534 may be used where the destination element is coupled to and extends up from conduit 1504 and bends towards the left. In addition to permitting an earlier exit from conduit 1504, beveled distal end 1532 also minimizes situations where a bend in the destination element, for example a conduit or blood vessel, causes the inside surface of the vessel to become constricted or reduced.

Figure 13:
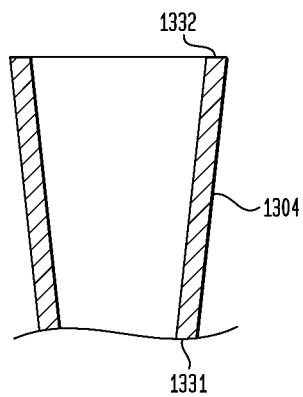
FIG. 13 is a cross-sectional view of a second interface according to one embodiment of the present invention in which the outer diameter increases while the wall thickness of the second interface remains substantially constant.

In yet further embodiments of the present invention, where the source body space and the destination element have different outside diameters, the outside diameters may be configured to accommodate the different outside diameters. As illustrated in FIG. 13, according to one such embodiment of the present invention, the outside diameter of conduit 1304 may vary from its proximal end 1331 to its distal end 1332. As shown, the inside diameter of conduit 1304 may also increase at the same rate as the change in the outside diameter of conduit 1304. However, it is to be understood that in other embodiments of the present invention, the inside diameter may change at a different rate, or not at all, as the change in the outside diameter.

Figure 17A:
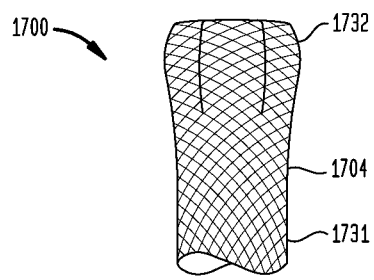
FIG. 17A is a perspective view of the second interface of a flow connector according to one embodiment of the present invention in its naturally collapsed state prior to implantation.
Figure 17B:
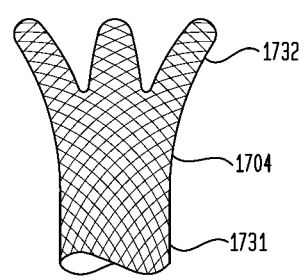
FIG. 17B is a perspective view of the second interface of a flow connector according to one embodiment of the present invention in its expanded state after implantation and forced expansion.

As shown in FIGS. 17A, B, and 18A, B, according to other embodiments of the present invention, flow connector 1700 and 1800 may be configured to be collapsible (FIGS. 17A, B) or expandable (FIGS. 18A, B) to further accommodate differences in the inside diameters of the source body space and the destination element. Furthermore, the collapsible and expandable embodiments may be used to assist implantation by implanting conduit 1704, 1804 while having a reduced physical size and then being force (or being allowed) to take on a larger shape to fit, for example seal and retain, the destination or source body space. Conduits 1704 and 1804 may be composed of a mesh material which has various joints or hinges or other manipulable series of parts which permit the overall shape of conduit 1704 and 1804 to be manipulated. Expandable conduit 1704 may be configured to with a small cross-sectional shape, as illustrated in FIG. 17A and later forced to take on and retain an expanded cross-sectional shape, as illustrated in FIG. 17B. In one embodiment of the present invention, expandable conduit 1704 may be expanded with a balloon inserted into implanted conduit 1704 and expanded. In another embodiment of the present invention, expandable conduit 1704 may have a mechanical expanding force applied at a proximal end 1731 which is communicated through the expanding portion of conduit 1704 in order to open conduit 1704 as illustrated in FIG. 17B. In the embodiment illustrated, conduit 1704 comprises finger-like portions which overlap one another as illustrated in FIG. 17A but which expand and separate as illustrated in FIG. 17B. It is to be understood that a portion of the finger-like portions may be used to retain the destination body space while a different portion may be used to provide a seal between conduit 1704 and the destination body space.

Figure 18A:
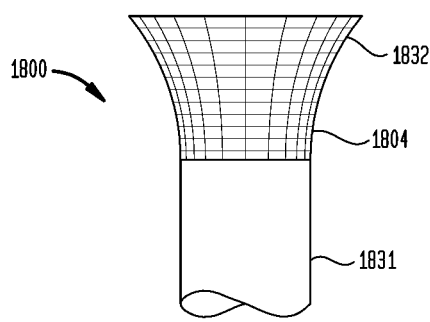
FIG. 18A is a perspective view of the second interface of a flow connector according to yet another embodiment of the present invention in its naturally expanded state prior to implantation.
Figure 18B:
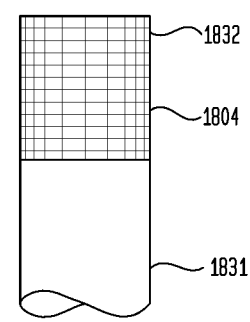
FIG. 18B is a perspective view of the second interface of a flow connector according to yet another embodiment of the present invention in its forced collapsed state, ready for implantation in the recipient.

Similarly, collapsible conduit 1804 may be configured with a shape-memory material, in a mesh or other configuration, which is expanded at rest but can be made to collapse when sufficient force is applied to it. As shown in FIGS. 18A, B, a portion of conduit 1804 may comprise the collapsible portion while another portion may be a non-collapsible portion. In one embodiment of the present invention, collapsible conduit 1804 may be disposed in a delivery tube (not shown) which is configured to receive conduit 1804 in a collapsed position before being inserted and then delivered in a destination body space. In another embodiment of the present invention, delivery tube (not shown) may be made of a resorbable material such that collapsible conduit 1804 may be delivered into the destination body conduit within the resorbable delivery tube. Subsequent to delivery, the resorbable delivery tube begins to be resorbed and cause the collapsible conduit 1804 to be released and permitted to return to its naturally expanded configuration.

Figure 11A:
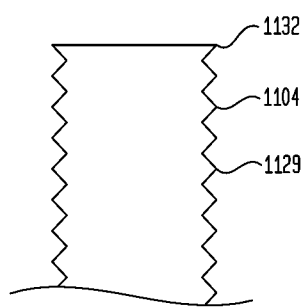
FIG. 11A illustrates a simplified schematic view of a portion of the second interface according to one embodiment of the present invention.
Figure 11B:
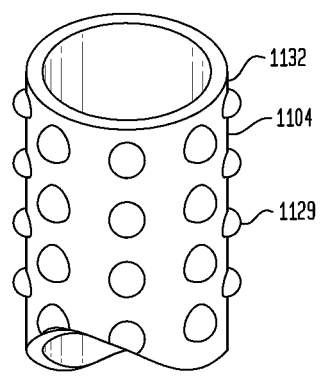
FIG. 11B illustrates a perspective view of a portion of the second interface according to a further embodiment of the present invention.
Figure 11C:
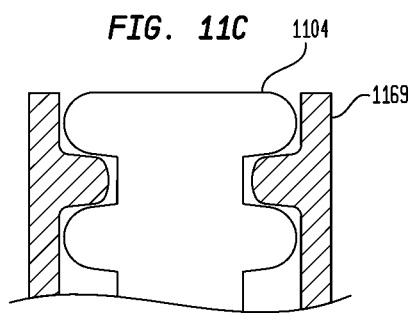
FIG. 11C illustrates a cross-sectional view of a portion of the second interface according to another embodiment of the present invention.
Figure 11D:
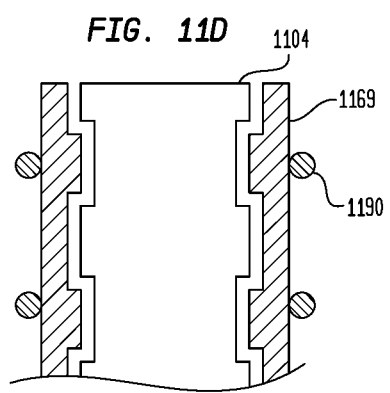
FIG. 11D illustrates a cross-sectional view of a portion of the second interface according to a yet further embodiment of the present invention.
Figure 11E:
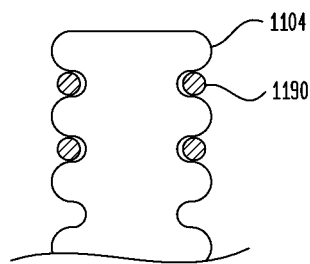
FIG. 11E illustrates a cross-sectional view of a portion of the second interface according to another embodiment of the present invention.
Figure 11F:
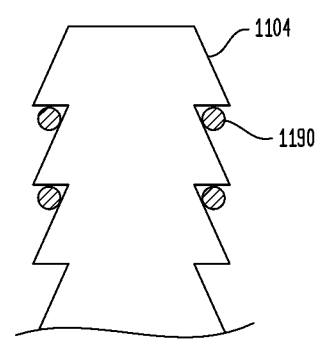
FIG. 11F illustrates a cross-sectional view of a portion of the second interface according to yet another embodiment of the present invention.
Figure 11G:
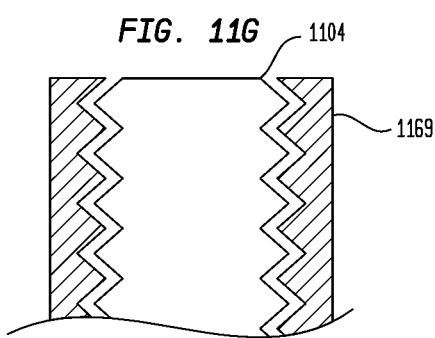
FIG. 11G illustrates a cross-sectional view of a portion of the second interface according to a further embodiment of the present invention.
Figure 11H:
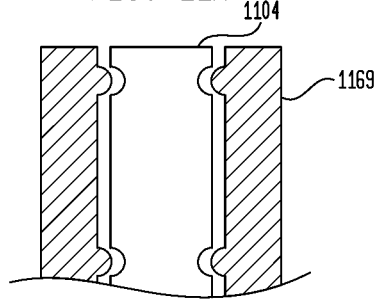
FIG. 11H illustrates a cross-sectional view of a portion of the second interface according to a yet further embodiment of the present invention.
Figure 11I:
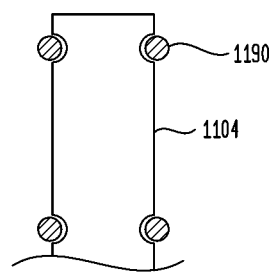
FIG. 11I illustrates a cross-sectional view of a portion of the second interface according to another embodiment of the present invention.
Figure 11J:
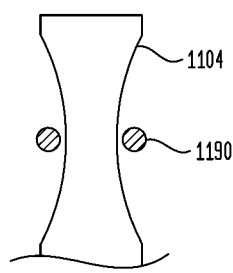
FIG. 11J illustrates a cross-sectional view of a portion of the second interface according to yet another embodiment of the present invention.
Figure 11K:
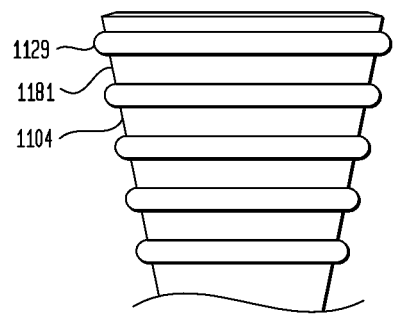
FIG. 11K illustrates a perspective view of a portion of the second interface according to one embodiment of the present invention.
Figure 11L:
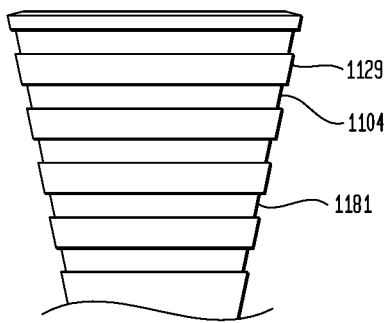
FIG. 11L illustrates a perspective view of a portion of the second interface according to another embodiment of the present invention.

According to embodiments of the present invention, as illustrated in FIGS. 11K and 11L, conduit 1104 may be modified or reduced subsequent to factory manufacturing. For example, according to one embodiment of the present invention, conduit 1104 is configured to allow a surgeon in vivo to evaluate the opening in the destination element, for example a vein, into which the distal end of conduit 1104 is to be inserted. After mentally or physically marking where the at or around which conduit 1104 is to be reduced, the surgeon cuts away material from distal end 132 in order to better fit flow connector 100 into the destination element. In other embodiments of the present invention, conduit 1104 may be configured with perforations adjacent one or more recesses 1181 or visual markers such as protrusions 1129 which can aid in the measuring of the portion to be cut or removed. In certain embodiments of the present invention, markers on the outside of conduit 1104 facilitate cutting of conduit 1104 at increments of 0.25 mm, 0.5 mm or 1.0 mm, or variations thereof. In other embodiments of the present invention, perforations along conduit 1104 are provided to facilitate in the cutting or otherwise modifying conduit 1104 at those increments of 0.25 mm, 0.5 mm or 1.0 mm, or variations thereof. Conduit 1104 may be constructed of a material that is resiliently flexible, such as silicone or other materials that are resiliently flexible, as will be appreciated by a person having ordinary skill in the art. Alternatively, conduit 1104 may be constructed of one or more materials so as to be rigid or hard, thus necessitating different tools in order to reduce or otherwise modify it than in embodiments of the present in which conduit 1104 is resiliently flexible.

Additionally, certain embodiments of the present invention may have one or more active elements in conduit 104 or flange 102 which are configured and arranged to provide one or more therapeutic benefits. For example, in one embodiment of the present invention, flow connector 100 is constructed of a material so that one or more portions of flow connector 100 is radiopaque. In other embodiments of the present invention, the active element is one or more drug compounds or pharmaceutical materials configured to be released by flow connector 100 and to act on into the area near the flow connector or systemically throughout the recipient. In certain embodiments of the present invention, the one or more pharmaceutical materials may be configured to require heat or fluid-contact activation in order to begin its being released. In other embodiments of the present invention, the pharmaceutical materials on flow connector 100 is further configured to be time-released such that the compounds therein are released gradually over a period of time at a constant or varying rates of release. In yet further embodiments of the present invention, the active element comprises pharmaceutical materials disposed within a heat or fluid-contact activated dissolving capsule shell.

As shown in FIG. 12B, other embodiments of the present invention may comprise a malleable conduit 1204 configured to take on and hold a different configuration upon receiving sufficient external force. For example, in one embodiment of the present invention, the surgeon may apply a bending force to conduit 1204 in order to accommodate the source and destination body conduits. Upon receiving sufficient bending force from the surgeon, conduit 1204 will retain the bend and direct or channel fluid flowing therethrough according to the shape, specifically the internal surface, of conduit 1204. Malleable conduit 1204 is configured from a mesh or other structure having cooperating elements such as shape memory metals which allow malleable conduit 1204 to retain a shape upon receiving the bending force described.

Figure 11M:
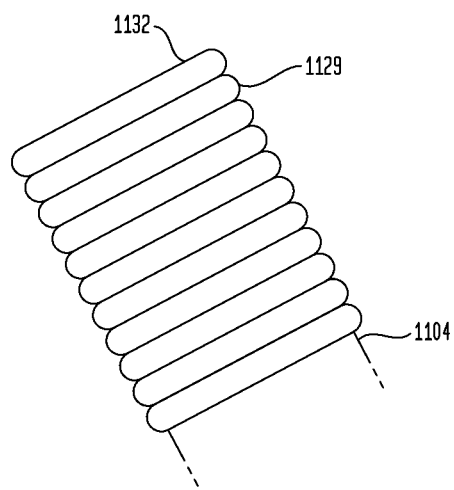
FIG. 11M illustrates a perspective view of a portion of the second interface according to yet another embodiment of the present invention.

Embodiments of the present invention may be configured to aid in the retention of the destination element (not shown) on the distal end 1132 of conduit 1104. In certain embodiments of the present invention, as illustrated in FIGS. 11A and 11B, protrusions 1129 are disposed circumferentially around the exterior surface of conduit 1104. FIG. 11A illustrates conduit 1104 in a simplified profile view, and shows the silhouette of radial protrusions 1129 which are disposed around conduit 1104. FIG. 11B illustrates a plurality of extrusions or projections which are disposed on, or extend from, the exterior of conduit 1104. As shown in FIG. 11M, according to another embodiment of the present invention, a plurality of radial protrusions 1129 on conduit 1104 may be provided along the substantial length of conduit 1104, or at least along a section, for example distal end section 1132. According to another embodiment of the present invention, protrusions 1129 may be disposed on a separate collar and positioned on conduit 1104 prior to implantation of flow connector 1100. As illustrated in FIGS. 11P and 11Q, the retention protrusions 1129 need not be uniform or simple. A matrix protrusion configuration 1129 is illustrated in FIG. 11P, according to another embodiment of the present invention. In a yet further embodiment of the present invention, sinusoidal protrusions 1129 are illustrated in FIG. 11Q.

In other embodiments of the present invention, the retention feature provided on the surface of conduit 1104 may be surface treatments. In an exemplary embodiment of the present invention illustrated in FIG. 11O, the exterior surface of conduit 1104 may be dimpled or dented such that the treated exterior surface provides retention. Depending on the size of the dimpling or denting surface treatment, the exterior surface can be configured to provide a friction fit on the interior surface of the destination element, for example a blood vessel. Other retention features may be provided on the exterior of conduit 1104. For example, in another embodiment of the present invention, a plurality of barbs 1229 or other sharp projections are disposed on the exterior of conduit 1204. Barbs 1229 are configured such that they at least partially pierce the wall of the destination element, for example a blood vessel, in order to retainingly secure the element on conduit 1204. In other embodiments of the present invention, barbs 1229 pierces through the destination element while retainingly securing the destination element on conduit 1204.

Flow connector 100, 200 further comprises a rest surface 136, 236 on conduit 104 adjacent the joint region 106, as illustrated in FIGS. 1D and 2B according to yet further embodiments of the present invention. In the embodiment illustrated in FIG. 1D, rest surface 136 is a recess in the body of conduit 104 configured to receive a wall of the source body space around rest surface 136 once flange 102 is implanted therein. In the embodiment illustrated, rest surface 136 is substantially smooth and free of protrusions 129 described above which are configured to retain the destination element once the destination element is positioned over protrusions 129. In the embodiment illustrated in FIGS. 1D and 2B, rest surface 136 is shaped with a curve, and source body space 227 is shown in FIG. 2B as conforming to the curved shape of rest surface 136. However, the degree to which body space 227 is shown to curve in FIG. 2B is exaggerated for illustrative purposes and may not always take the degree of curvature depicted.

Figure 11N:
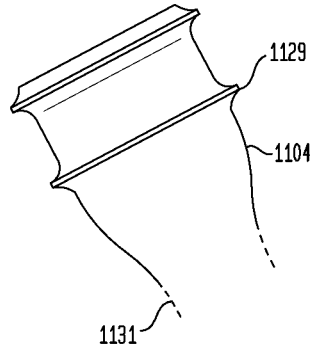
FIG. 11N illustrates a perspective view of a portion of the second interface according to a yet further embodiment of the present invention.
Figure 11O:
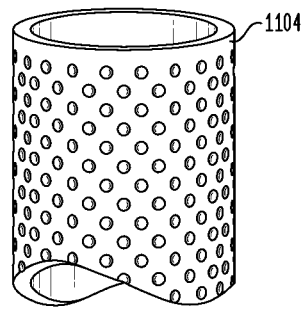
FIG. 11O illustrates a perspective view of a portion of the second interface according to another embodiment of the present invention.
Figure 11P:
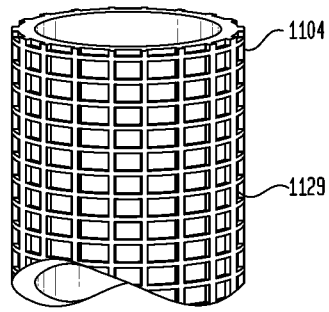
FIG. 11P illustrates a perspective view of a portion of the second interface according to yet another embodiment of the present invention.
Figure 11Q:
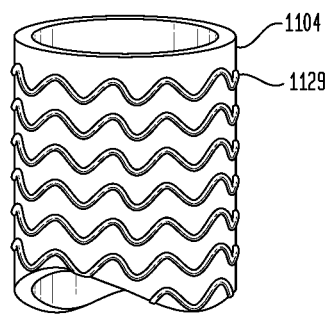
FIG. 11Q illustrates a perspective view of a portion of the second interface according to a further embodiment of the present invention.

In addition to the protrusions described above being used to retain the destination element upon being fit on the protrusions, the protrusions may also be used to receive one or more retaining elements such as sutures or a securing collar, or combinations thereof, as in embodiments illustrated in FIGS. 10E, 11A-11N. FIG. 10E illustrates one embodiment of the present invention in which two sutures are placed on the destination element, in this case a vein, in order to compress the vein towards recesses disposed along the exterior surface of conduit 1004. FIG. 11A illustrates one embodiment in which the plurality of adjacent protrusions 1129 cooperatively form angled recess therebetween into which retaining elements such as sutures 1190, as illustrated in FIGS. 11E, 11F, 11I, 11J, can compress the destination element at least partly into. In the embodiment illustrated in FIG. 11B, the retaining elements can compress the destination element, such as the tissue wall of a vein, in between the spaces between protrusions 1129. In the embodiments of the present invention illustrated in FIGS. 11C, 11D, 11G, 11H, a securing collar 1169 may be used with a portion of the destination element, for example the tissue wall of a vein, disposed between securing collar 1169 and conduit 1104 to secure the destination element on conduit 1104. In certain embodiments of the present invention, the destination element portion may be compressed by securing collar 1169 against the exterior surface of conduit 1104. In other embodiments of the present invention, securing collar 1169 may press the destination element portion into correspondingly shaped recesses along the exterior surface of conduit 1104 such that an interference fit between the recesses and securing collar 1169 will retain the destination element portion on conduit 1104. Although a plurality of protrusions 1129 may be disposed along a length of conduit 1104 according to certain embodiments of the present invention, such that a surgeon may have a wide variety of choices of protrusions 1129 to use in order to secure the destination element on conduit 1104, protrusions 1129 may also be provided at distinct locations in order to simplify conduit 1104, where the surgeon is provided with a reduced number of protrusions 1129, for example two as shown in FIG. 11N according to one embodiment of the present invention. As shown in FIG. 11N, protrusions 1129 may flare out from a smooth exterior surface of conduit 1104 such that a securing element such as sutures 1190, configured with a smaller diameter than protrusions 1129, may be placed nearer the proximal end 1131 of conduit 1104 such that an interference fit is formed between sutures 1190 and protrusions 1129. In such embodiments, in addition to the one or more sutures acting to retain the destination element on conduit 1104, the flare at the distal end of conduit 1104 itself may be sufficient to provide a compression fit to also retain the destination element on conduit 1104. Such a compression fit also acts to provide a seal to prevent leakage flowing through conduit 1104 into the destination element. In alternative embodiments of the invention, flare portions 1129 (referred to previously as protrusions 1129) may be constructed as a separate component from conduit 1104 such that conduit 1104 can rotate 360° about a longitudinal axis of flare portion 1129 while flare portion 1129 remains stationary and secure to the destination element.

It is to be understood that embodiments of the present invention may be used to connect flow connector described herein with an artificial conduit 1999, as illustrated in FIG. 19. As shown, a first flow connector 1900 is configured to be coupled to artificial conduit 1999 and retained by securing collar parts 1269A, B. Securing collar parts 1269A, B combine to form securing collar 1269. Securing collar parts 1269A, B each may be configured with a retention feature such as the recess shown for fitting around a correspondingly configured protrusion on the exterior of conduit. In the embodiment illustrated in FIG. 19, each end of artificial conduit 1999 is positioned between each of the conduits 1904 and retaining collars 1269, wherein each of the flanges 1902 of the flow connectors are implanted without the same or different body spaces, such that the flow connectors 1900 become fluidically coupled. In this manner, flow connectors 1900 may be used in bypass or other procedures which can benefit from one or more flanges which provide fluidic coupling as well as self-sealing and self-supporting features, among others.

It is to be understood that although embodiments of the present invention have been largely described as being used to connect two tissue-enclosed body spaces, for example veins and arteries, other embodiments of the present invention may be used to connect a body space to an artificial device, such as a pump, an artificial conduit connected to the flow connector 100 conduit 102, sensors, plugs, among others.

The invention described and claimed herein is not to be limited in scope by the specific preferred embodiments herein disclosed, since these embodiments are intended as illustrations, and not limitations, of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

What is claimed is:

1. An implantable flow connector for fluidically coupling a tissue-enclosed source body space with a destination element, comprising:

a conduit having a lumen terminating at an orifice at a first end of the conduit implantable in the source body space through an opening formed in a tissue wall of the source body space, and a second end of the conduit implantable in the destination element through an opening in a surface of the destination element; and a circumferential flexible flange, radially extending from the conduit proximate the conduit first end, configured to be implanted in the source body space adjacent an opening in the tissue wall of the source body space such that the conduit extends through the opening, the flange comprising first and second longitudinal sections extending on first and second opposing sides of the conduit and first and second lateral sections extending on third and fourth opposing sides of the conduit, the longitudinal and lateral sections each having an inner section closer to the conduit and an outer section positioned radially outward of the inner section and further from the conduit than the inner section, wherein adjacent lateral and longitudinal sections are joined at the outer sections to form a continuous flange with a continuous outer edge, the lateral sections configured to extend around a longitudinal axis of the source body space and configured to cooperate with the walls of the body space such that the flange sealingly conforms to an inner surface of the tissue wall adjacent the opening in the body space.

2. The flow connector of claim 1, wherein said destination element is a destination tissue-enclosed body space.

3. The flow connector of claim 2, wherein the opening in the destination is an artificial opening in a tissue wall of the destination body space.

4. The flow connector of claim 2, wherein the artificial opening is an orifice at a severed end of the destination.

5. The flow connector of claim 2, wherein said flow connector conduit has an outside diameter that is substantially the same as an inside diameter of a region of said destination element into which the flow connector conduit is implanted.

6. The flow connector of claim 1, wherein said destination element is a medical device.

7. The flow connector of claim 1, wherein said lumen is non-cylindrical.

8. The flow connector of claim 1, wherein said conduit and said flange are formed as separate parts and joined together.

9. The flow connector of claim 1, further comprising one or more cutout regions disposed on said flange and configured to promote folding of said flange to facilitate insertion through the opening.

10. The flow connector of claim 1, wherein outer edges of said flange are chamfered.

11. The flow connector of claim 1, wherein a longitudinal axis of said lumen in said conduit is disposed at an angle of approximately 10° to 90° with respect to a longitudinal axis of said flange.

12. The flow connector of claim 11, wherein the longitudinal axis of said lumen in said conduit is disposed at an angle of approximately 60° with respect to the longitudinal axis of said flange.

13. The flow connector of claim 1, wherein said lateral sections taper from an imaginary plane flush with the conduit orifice, by a taper angle greater than 0° from said plane.

14. The flow connector of claim 13, wherein said taper angle of said longitudinal sections from said imaginary plane is approximately 10°.

15. The flow connector of claim 1, wherein the lateral sections are memory material and have a radius of curvature greater that the radius of curvature of the source body space.

16. The flow connector of claim 1, wherein the flow connector is configured such that it is urged out of the opening of the source body space by forces generated by said lateral sections being disposed against the tissue wall.

17. The flow connector of claim 1, wherein the flange comprises one or more circumferentially adjacent sections at least one of which has a rigidity that decreases as the radial distance of the flange from the conduit increases.

18. The implantable flow connector of claim 17, wherein said one or more circumferentially adjacent sections comprise:

a first section having a first rigidity; and a second section having a second rigidity, wherein the rigidity of said first section is greater than the rigidity of said second section.

19. The implantable flow connector of claim 18, wherein a composition of said first and second sections are substantially similar and further wherein a thickness of said first and second sections are different.

20. The implantable flow connector of claim 17, wherein a composition of said first and second sections are different and further wherein a thickness of said first and second sections are substantially similar.

21. The implantable flow connector of claim 17, wherein said first section is proximal the conduit and said second section is distal the conduit with respect to said first section.

22. The implantable flow connector of claim 17, wherein said one or more circumferentially adjacent sections form a continuous surface around said conduit.

23. The implantable flow connector of claim 1, wherein the flange comprises one or more circumferentially adjacent sections constructed and arranged to reinforce the conduit.

24. The implantable flow connector of claim 23, wherein said one or more circumferentially adjacent sections comprise:
a first section having a first rigidity; and
a second section having a second rigidity,
wherein the rigidity of said first section is greater than the rigidity of said second section and is sufficient to reinforce said conduit.

25. The implantable flow connector of claim 1, further wherein the cooperation of the lateral sections and the tissue wall urge the flow connector toward the opening thereby causing the flow connector to be supported by the flange sections.

26. The implantable flow connector of claim 25, wherein said lateral sections are configured to collectively extend into the body space at least up to a point along the tissue wall having a largest diameter in the body space when said flange is implanted in the source body space to its operative position.

27. The implantable flow connector of claim 25, wherein said lateral sections are configured to collectively extend into the body space to approximately 180° of the circumference of the body space when said flange is implanted in the source body space to its operative position.

28. The implantable flow connector of claim 1, wherein the flange comprises one or more circumferentially adjacent sections constructed and arranged to substantially retain the flow connector in a substantially stationary operable position within the source body space.

29. The implantable flow connector of claim 1, wherein the flange comprises one or more circumferentially adjacent sections each having a combination of one or more of composition and dimensions that prevents the lateral sections from substantially deflecting in response to explant forces exerted on the flow connector.

30. The implantable flow connector of claim 29, wherein one of said one or more circumferentially adjacent sections has a maximum length from said conduit of approximately 25% to 100% of an outside diameter of said conduit, wherein said length is along a longitudinal axis of a region the body space in which said flange is to be implanted.

31. The implantable flow connector of claim 29, wherein one of said one or more circumferentially adjacent sections has a maximum length from said conduit of approximately 35% to 85% of an outside diameter of said conduit, wherein said length is along a longitudinal axis of a region the body space in which said flange is to be implanted.

32. The implantable flow connector of claim 29, wherein one of said one or more circumferentially adjacent sections has a maximum length from said conduit of approximately 50% of an outside diameter of said conduit, wherein said length is along a longitudinal axis of a region the body space in which said flange is to be implanted.

33. The implantable flow connector of claim 29, wherein the one or more circumferentially adjacent sections of said flange comprise:
a first section having a first thickness; and
a second section having a second thickness,
wherein the first thickness is different from the second thickness.

34. The implantable flow connector of claim 33, wherein one of at least said first and second thicknesses is substantially equal to a thickness of the wall tissue of the source body conduit.

35. The implantable flow connector of claim 34, wherein one of at least said first and second thicknesses is approximately 0.2 mm to approximately 1.0 mm.

36. The implantable flow connector of claim 35, wherein one of at least said first and second thicknesses is approximately 0.5 mm.

37. The implantable flow connector of claim 36, wherein the thickness of said first section is approximately 50% to approximately 100% of the thickness of said second section.

38. The implantable flow connector of claim 29, wherein the one or more circumferentially adjacent sections of said flange comprise:
a first section having a first composition; and
a second section having a second composition,
wherein the first composition is different from the second composition.

39. The implantable flow connector of claim 38, wherein one of at least said first and second compositions has a shore value of 80A.

40. The implantable flow connector of claim 39, wherein the other of at least said first and second compositions has a shore value of 55D.

41. The implantable flow connector of claim 38, wherein said first and second compositions each have a softness corresponding to a shore value between 80A and 55D.

42. The implantable flow connector of claim 1, wherein the lateral sections cooperate with the tissue wall to urge the flow connector out of the opening thereby causing the flange to sealingly abut the inner surface of the source body conduit.

43. An implantable flow connector configured to fluidically couple a tissue-enclosed source body space with a destination element, comprising:
an elongate body including a fluid channel extending therethrough and implantable in the destination element; and
a flexible flange extending from the elongate body proximate an end of the elongate body, the flange being configured to be implanted in the source body space adjacent an opening formed in a tissue wall such that the fluid channel fluidically couples fluid in the source tissue-enclosed body space with the destination element, wherein
the flange includes first and second lateral sections and a contact surface configured to interface with an interior of the tissue wall of the source body space, and
wherein the flange is configured upon implantation to exert an outward force on the interior of the tissue wall so as to cause the wall of the source body to resist the outward force to thereby provide a compression force to the lateral sections to urge the contact surface of the flange toward the opening so as to provide a seal between the contact surface and the tissue wall without a force applied by an external device against an exterior of the tissue wall such that fluid within the source body space will not leak out the opening formed between the tissue wall of the source body space and an exterior of the implantable flow connector.

44. The implantable flow connector of claim 43, wherein: the seal is a hydrophobic seal.

45. The implantable flow connector of claim 43, further comprising longitudinal sections contiguous with the lateral sections.

46. The implantable flow connector of claim 45, wherein: elongate body and the flange are a monolithic structure.

47. The implantable flow connector of claim 45, further comprising:
a securing element configured to extend around the elongate body configured to secure the destination element thereto.

48. The implantable flow connector of claim 47, wherein the conduit includes a plurality of radial protrusions and the securing element engages the protrusions on an external surface of the conduit.

49. The implantable flow connector of claim 43, wherein the flange comprises one or more circumferentially adjacent sections constructed and arranged to reinforce the conduit.

50. The implantable flow connector of claim 43, further comprising first and second longitudinal sections contiguous with the lateral sections.

51. The implantable flow connector of claim 50, wherein the first and second longitudinal sections have different lengths.

52. A method of fluidically coupling a source tissue-enclosed body space with a destination element, comprising:
obtaining access to an opening in a tissue wall of the source body space;
inserting a flange portion of an implantable flow connector through the opening and into the source body space such that a conduit within the flow connector is implanted in the destination element for fluid communication with an interior of the source body space;
establishing a seal between the implantable flow connector and the tissue wall such that fluid within the source body space will not leak out an area between the opening in the tissue wall of the source body space and an exterior of the implantable flow connector by enabling a portion of the implantable flow connector located within the source body space to exert a force against the tissue wall, said force being substantially primarily generated by the portion of the implantable flow connector in the source body space without a reacting force generated on an outside of the tissue wall.

53. The method of claim 52, wherein:
said force consists of force generated by the portion of the implantable flow connector in the source body space.

54. The method of claim 52, wherein:
the seal is established without an additional component that interfaces with the tissue wall.

55. The method of claim 52, wherein:
the implantable flow connector is a monolithic device; and
the seal is established with only the implantable flow connector interfacing with the tissue wall.

56. The method of claim 52, wherein:
the force is generated solely by a flange of the implantable flow connector implanted within the source body space.

57. The method of claim 52, wherein the force is generated by a flange of the implantable flow connector, the flange having a radius of curvature lying on a plane, the method further comprising:
selecting the implantable flow connector such that the radius of curvature of the flange is greater than a radius of curvature of the interior wall of the source body space lying on the plane when the implantable flow connector is located therein.

58. The method of claim 52, wherein:
after the flow connector is inserted through the opening into the source body space, the flow connector is urged out of the opening of the source body space by the exerted force.

59. An implantable flow connector for fluidically coupling a tissue-enclosed source body space with a destination element, comprising:
a conduit having a lumen terminating at an orifice at a first end of the conduit implantable in the source body space through an opening formed in a tissue wall of the source body space, and a second end of the conduit implantable in the destination element through an opening in a surface of the destination element; and
a circumferential flexible flange, radially extending from the conduit proximate the conduit first end, configured to be implanted in the source body space adjacent an opening in the tissue wall of the source body space such that the conduit extends through the opening, the flange comprising first and second lateral sections configured to extend around the longitudinal axis of the source body space and configured to cooperate with the walls of the body space such that the flange sealingly conforms to the inner surface of the tissue wall adjacent the opening in the body space to provide a sealing region, and a reinforcement region adjacent the sealing region to reinforce the flow connector.

60. The implantable flow connector of claim 59, wherein the reinforcement region has a rigidity to aid in opposition of deflection forces.

61. The implantable flow connector of claim 60, wherein the rigidity of the reinforcement region decreases in a radially increasing direction with respect to the conduit.

62. The implantable flow connector of claim 59, wherein the reinforcement region is composed of a material of a greater durometer than the sealing region.

63. The implantable flow connector of claim 59, wherein the reinforcement region has a thickness greater than adjacent regions of the flange.

64. The implantable flow connector of claim 59, wherein the reinforcement region is proximal to the conduit to provide structural integrity to the conduit.

65. The implantable flow connector of claim 59, wherein the reinforcement region comprises multiple regions extending circumferentially around the conduit.

66. The implantable flow connector of claim 59, wherein the reinforcement region is contiguous.

67. The implantable flow connector of claim 59, wherein the reinforcement region has a perimeter similar to a perimeter of the flange.

68. The implantable flow connector of claim 59, wherein the lateral sections when implanted in the source body space form an angle to an imaginary plane flush with the conduit orifice.

69. The implantable flow connector of claim 59, wherein the reinforcement region extends around the conduit.

* * * * *